US009877732B2

(12) United States Patent
Raybin et al.

(10) Patent No.: US 9,877,732 B2
(45) Date of Patent: Jan. 30, 2018

(54) HEMOSTATIC CLIP WITH NEEDLE PASSER

(71) Applicant: Boston Scientific Scimed, Inc., Maple Grove, MN (US)

(72) Inventors: Samuel Raybin, Marlborough, MA (US); Paul Smith, Smithfield, RI (US); Norman C May, Northborough, MA (US); Naroun Suon, Lawrence, MA (US); Matthew Jagelski, West Roxbury, MA (US); Ray Hewenson Tong, Milford, MA (US); John B. Golden, Norton, MA (US); Kevin James McElwee, Franklin, MA (US); Andrew James Whitney, Douglas, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 214 days.

(21) Appl. No.: 14/788,021

(22) Filed: Jun. 30, 2015

(65) Prior Publication Data
US 2016/0000445 A1 Jan. 7, 2016

Related U.S. Application Data

(60) Provisional application No. 62/019,588, filed on Jul. 1, 2014.

(51) Int. Cl.
*A61B 17/04* (2006.01)
*A61B 17/122* (2006.01)
(Continued)

(52) U.S. Cl.
CPC .... *A61B 17/1227* (2013.01); *A61B 17/00234* (2013.01); *A61B 17/0469* (2013.01);
(Continued)

(58) Field of Classification Search
CPC ............ A61B 17/0467; A61B 17/0469; A61B 17/0485; A61B 17/0487; A61B 17/062;
(Continued)

(56) References Cited

U.S. PATENT DOCUMENTS 3,958,576 A * 5/1976 Komiya ............... A61B 17/083
24/456
5,181,919 A * 1/1993 Bergman ........... A61B 17/0469
606/139
(Continued)

FOREIGN PATENT DOCUMENTS

EP 2 462 877 6/2012
JP 2009279395 12/2009

*Primary Examiner* — Ryan J Severson
(74) *Attorney, Agent, or Firm* — Fay Kaplun & Marcin, LLP

(57) ABSTRACT

A device for treating a tissue opening includes a proximal portion including an elongated flexible member, a capsule releasably coupled to a distal end of the flexible member and including a lumen extending therethrough and a clip including a pair of arms movably housed within the capsule. A suture extending along a first one of the pair of arms and including a loop at a distal end thereof extending across an opening extending through the first one of the pair of arms. A suture grabbing element extending laterally from a second one of the pair of arms and including a hook so that, when the pair of arms are moved toward a closed configuration, the hook extends through the opening to grab the loop and draw the distal end of the suture from the first one of the pair of arms toward the second one of the pair of arms.

18 Claims, 15 Drawing Sheets

(51) Int. Cl.
*A61B 17/062* (2006.01)
*A61B 17/00* (2006.01)
*A61B 17/08* (2006.01)
*A61B 17/10* (2006.01)
*A61B 17/128* (2006.01)
*A61B 17/06* (2006.01)
*A61B 90/00* (2016.01)

(52) U.S. Cl.
CPC ........ *A61B 17/062* (2013.01); *A61B 17/0625* (2013.01); *A61B 17/083* (2013.01); *A61B 17/10* (2013.01); *A61B 17/1285* (2013.01); *A61B 17/0467* (2013.01); *A61B 2017/00278* (2013.01); *A61B 2017/00353* (2013.01); *A61B 2017/00358* (2013.01); *A61B 2017/06047* (2013.01); *A61B 2017/086* (2013.01); *A61B 2090/037* (2016.02)

(58) Field of Classification Search
CPC ... A61B 17/0625; A61B 17/08; A61B 17/083; A61B 17/10; A61B 17/122; A61B 17/1227; A61B 17/128; A61B 17/1285; A61B 2017/00349; A61B 2017/00353; A61B 2017/047; A61B 2017/0475; A61B 2017/0477; A61B 2017/0488; A61B 2017/0496; A61B 2017/081; A61B 2090/037
See application file for complete search history.

(56) References Cited

U.S. PATENT DOCUMENTS

| | | | | |
|---|---|---|---|---|
| 5,304,183 A * | 4/1994 | Gourlay | ........... | A61B 17/00234 227/901 |
| 5,454,823 A * | 10/1995 | Richardson | ........ | A61B 17/0469 606/145 |
| 5,522,820 A * | 6/1996 | Caspari | ............... | A61B 17/0625 606/139 |
| 5,690,653 A * | 11/1997 | Richardson | ........ | A61B 17/0469 606/148 |
| 5,730,747 A * | 3/1998 | Ek | .................... | A61B 17/0469 606/139 |
| 5,947,982 A * | 9/1999 | Duran | ................. | A61B 17/0625 606/139 |
| 5,980,538 A * | 11/1999 | Fuchs | ................. | A61B 17/0469 606/139 |
| 7,357,805 B2 * | 4/2008 | Masuda | ............... | A61B 17/122 606/139 |
| 7,377,926 B2 * | 5/2008 | Topper | ............... | A61B 17/0469 606/144 |
| 7,381,212 B2 * | 6/2008 | Topper | ............... | A61B 17/0469 606/223 |
| 7,494,461 B2 * | 2/2009 | Wells | ................... | A61B 17/122 600/104 |
| 7,572,265 B2 * | 8/2009 | Stone | ................. | A61B 17/0625 606/139 |
| 7,931,578 B2 * | 4/2011 | Whayne | ............. | A61B 17/0401 600/16 |
| 7,972,344 B2 * | 7/2011 | Murray | ............... | A61B 17/0469 606/144 |
| 8,057,489 B2 * | 11/2011 | Stone | ................. | A61B 17/0469 606/139 |
| 8,177,794 B2 * | 5/2012 | Cabrera | ................. | A61B 17/04 606/144 |
| 8,246,637 B2 * | 8/2012 | Viola | ..................... | A61B 17/04 606/144 |
| 8,282,656 B2 * | 10/2012 | Hart | ................... | A61B 17/0469 606/139 |
| 8,292,905 B2 * | 10/2012 | Taylor | .................... | A61B 17/04 606/144 |
| 8,292,906 B2 * | 10/2012 | Taylor | .................... | A61B 17/04 606/144 |
| 8,337,515 B2 * | 12/2012 | Viola | ..................... | A61B 17/04 606/144 |
| 8,372,090 B2 * | 2/2013 | Wingardner | ........... | A61B 17/04 606/139 |
| 8,460,275 B2 * | 6/2013 | Taylor | .................... | A61B 17/04 227/176.1 |
| 8,460,318 B2 * | 6/2013 | Murray | ............... | A61B 17/0469 606/144 |
| 8,496,674 B2 * | 7/2013 | Cabrera | ................. | A61B 17/04 606/144 |
| 8,506,581 B2 * | 8/2013 | Wingardner, III | ..... | A61B 17/04 606/139 |
| 8,591,526 B2 * | 11/2013 | Cronin | ............... | A61B 17/0469 606/144 |
| 8,628,545 B2 * | 1/2014 | Cabrera | ............. | A61B 17/0469 606/144 |
| 8,636,752 B2 * | 1/2014 | Cabrera | ................. | A61B 17/04 606/144 |
| 8,747,424 B2 * | 6/2014 | Taylor | .................... | A61B 17/04 606/144 |
| 8,968,339 B2 * | 3/2015 | Malkowski | ....... | A61B 17/06066 606/144 |
| 8,968,340 B2 * | 3/2015 | Chowaniec | ........ | A61B 17/0469 606/144 |
| 8,968,342 B2 * | 3/2015 | Wingardner, III | ..... | A61B 17/04 606/139 |
| 8,986,326 B2 * | 3/2015 | Satake | .................... | A61B 17/08 606/142 |
| 9,113,860 B2 * | 8/2015 | Viola | ..................... | A61B 17/04 |
| 9,271,723 B2 * | 3/2016 | Taylor | .................... | A61B 17/04 |
| 9,393,010 B2 * | 7/2016 | Murray | ............... | A61B 17/0469 |
| 2003/0065337 A1 * | 4/2003 | Topper | ............... | A61B 17/0469 606/144 |
| 2004/0199184 A1 * | 10/2004 | Topper | ............... | A61B 17/0469 606/144 |
| 2005/0049618 A1 * | 3/2005 | Masuda | ............... | A61B 17/122 606/151 |
| 2005/0267529 A1 * | 12/2005 | Crockett | .......... | A61B 17/00234 606/215 |
| 2006/0004388 A1 * | 1/2006 | Whayne | ............. | A61B 17/0401 606/151 |
| 2006/0020162 A1 * | 1/2006 | Whayne | ............. | A61B 17/0401 600/37 |
| 2007/0093857 A1 * | 4/2007 | Rogers | ............... | A61B 17/0644 606/142 |
| 2007/0225735 A1 * | 9/2007 | Stone | .................. | A61B 17/0625 606/144 |
| 2008/0208221 A1 * | 8/2008 | Murray | ............... | A61B 17/0469 606/145 |
| 2008/0255427 A1 * | 10/2008 | Satake | .................... | A61B 17/08 600/204 |
| 2009/0306684 A1 * | 12/2009 | Stone | .................. | A61B 17/0469 606/145 |
| 2009/0312773 A1 * | 12/2009 | Cabrera | ............. | A61B 17/0469 606/144 |
| 2010/0010512 A1 * | 1/2010 | Taylor | .................... | A61B 17/04 606/144 |
| 2010/0030028 A1 * | 2/2010 | Cabrera | ................. | A61B 17/04 600/127 |
| 2010/0030238 A1 * | 2/2010 | Viola | ..................... | A61B 17/04 606/144 |
| 2010/0049219 A1 * | 2/2010 | Cronin | ............... | A61B 17/0469 606/144 |
| 2010/0076460 A1 * | 3/2010 | Taylor | .................... | A61B 17/04 606/144 |
| 2010/0076461 A1 * | 3/2010 | Viola | ..................... | A61B 17/04 606/144 |
| 2010/0094083 A1 * | 4/2010 | Taylor | .................... | A61B 17/04 600/106 |
| 2010/0121352 A1 * | 5/2010 | Murray | ............... | A61B 17/0469 606/144 |
| 2010/0137887 A1 * | 6/2010 | Crockett | .......... | A61B 17/00234 606/144 |

(56) References Cited

U.S. PATENT DOCUMENTS

| | | | | |
|---|---|---|---|---|
| 2010/0217282 A1* | 8/2010 | Cabrera | ............... | A61B 17/04 606/144 |
| 2010/0228270 A1* | 9/2010 | Bogart | ............... | A61B 17/0469 606/144 |
| 2010/0274265 A1* | 10/2010 | Wingardner | ........... | A61B 17/04 606/144 |
| 2010/0305581 A1* | 12/2010 | Hart | ............... | A61B 17/0469 606/139 |
| 2012/0150197 A1* | 6/2012 | Malkowski | ........ | A61B 17/0625 606/144 |
| 2012/0158020 A1* | 6/2012 | Crockett | .......... | A61B 17/00234 606/139 |
| 2012/0215234 A1* | 8/2012 | Chowaniec | ........ | A61B 17/0469 606/144 |
| 2012/0277769 A1* | 11/2012 | Cabrera | ............... | A61B 17/04 606/147 |
| 2013/0035703 A1* | 2/2013 | Taylor | ............... | A61B 17/04 606/144 |
| 2013/0110136 A1* | 5/2013 | Viola | ............... | A61B 17/04 606/145 |
| 2013/0123815 A1* | 5/2013 | Wingardner, III | ..... | A61B 17/04 606/145 |
| 2013/0261644 A1* | 10/2013 | Taylor | ............... | A61B 17/04 606/144 |
| 2013/0317525 A1* | 11/2013 | Wingardner, III | ..... | A61B 17/04 606/145 |
| 2013/0345725 A1* | 12/2013 | Murray | ............... | A61B 17/0469 606/147 |
| 2016/0000433 A1* | 1/2016 | Raybin | ............... | A61B 17/0469 606/145 |
| 2016/0000445 A1* | 1/2016 | Raybin | ............... | A61B 17/0469 606/157 |
| 2016/0174967 A1* | 6/2016 | Taylor | ............... | A61B 17/04 606/144 |

* cited by examiner

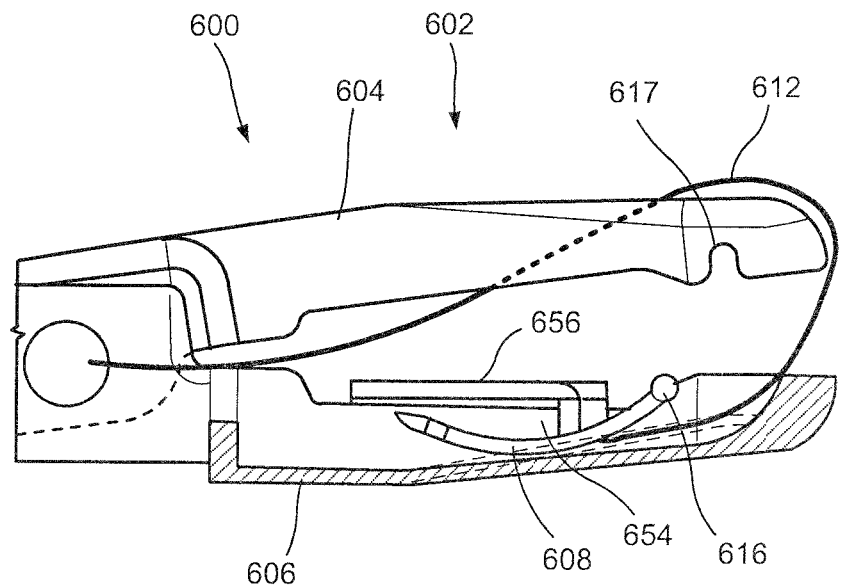
F I G. 26
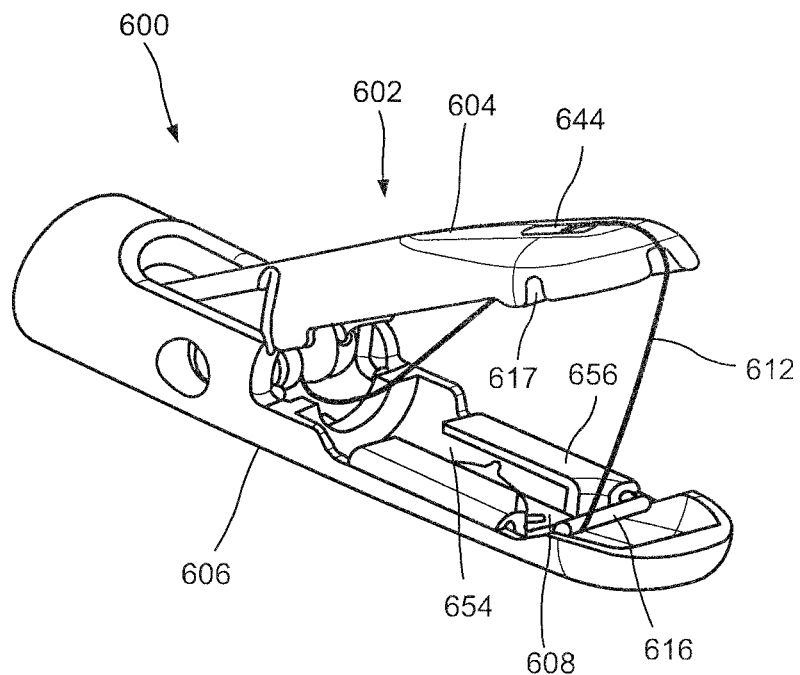
F I G. 27

HEMOSTATIC CLIP WITH NEEDLE PASSER

PRIORITY CLAIM

The present application is claims priority to U.S. Provisional Patent Application Ser. No. 62/019,588 filed Jul. 1, 2014; the disclosure of which is incorporated herewith by reference.

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may increase the risk of perforating the wall of the GI tract, or may require closure of the GI tract wall as part of the procedure. Endoscopic closure reduces cost and may reduce the trauma and inconvenience associated with these procedures. However, conventional tissue closure devices may be insufficient to close certain perforations.

SUMMARY

The present disclosure relates to a device for treating a tissue opening, comprising a proximal portion including an elongated flexible member, a capsule releasably coupled to a distal end of the flexible member, the capsule extending longitudinally from a proximal end to a distal end and including a lumen extending therethrough, and a clip including a pair of arms movably housed within the lumen of the capsule such that the pair of arms are movable between an open configuration and a closed configuration, the pair of arms being biased toward the open configuration such that when the pair of arms are moved distally with respect to the capsule, distal ends of the pair of arms are separated from one another to receive target tissue therebetween. The device also comprises a suture extending along a first one of the pair of arms and including a loop at a distal end thereof, the loop extending across an opening extending laterally through the first one of the pair of arms and a suture grabbing element extending laterally from a second one of the pair of arms toward the first one of the pair of arms and including a hook so that, when the pair of arms are moved toward the closed configuration, the hook extends through the opening in the first one of the pair of arms to grab the loop extending across the opening to draw the distal end of the suture from the first one of the pair of arms toward the second one of the pair of arms.

In an embodiment, the first one of the pair of arms may include a notch in communication with the opening so that the loop is received within the notch to extend across the opening.

In an embodiment, the notch may extend one of along an interior surface of the first one of the pair of arms and proximally from a distal edge of the first one of the pair of arms.

In an embodiment, the device may further comprise a control member connected to the pair of arms for moving the pair of arms between the open configuration and the closed configuration.

In an embodiment, the device may further comprising a locking mechanism for locking the pair of arms in the capsule in the closed configuration.

In an embodiment, the capsule may include a wedge feature wedging the suture between the wedge feature and a portion of one of the pair of arms, when the arms are locked within the capsule, so that the suture is restrained from distal translation.

In an embodiment, the capsule may further include a cutting feature cutting a portion of the suture extending proximally of a wedged portion of the suture.

In an embodiment, the first one of the pair of arms may include a second opening and the second one of the pair of arms includes a wedge element extending laterally therefrom toward the first one of the pair of arms so that, when the pair of arms are locked within the capsule, the wedge element extends through the second opening to wedge the suture between the wedge element and an edge of the second opening.

The present disclosure also relates to a device for treating a tissue opening, comprising a proximal portion including an elongated flexible member, a capsule releasably coupled to a distal end of the flexible member, the capsule extending longitudinally from a proximal end to a distal end and including a lumen extending therethrough and a clip including pair of arms movably housed within the lumen of the capsule such that the pair of arms are movable between an open configuration and a closed configuration, the pair of arms being biased toward the open configuration such that when the pair of arms are moved distally with respect to the capsule, distal ends of the pair of arms are separated from one another to receive target tissue therebetween. The device also comprises a needle extending from a first end pivotally connected to a first one of the pair of arms via a releasable connection to a second end, the needle pivotal relative to the first one of the pair of arms between an insertion configuration, in which the second end is moved toward the first one of the pair of arms, and a firing position, in which the second end extends laterally toward a second one of the pair of arms, so that, when the pair of arms are moved toward the closed configuration in the firing position, the needle engages an engaging feature along a second one of the pair of arms, the releasable connection releasing when the pair of arms are moved toward the open configuration after the needle has engage the engaging feature and a suture extending through a portion of the device such that a distal end thereof is connected to the needle.

In an embodiment, the needle may be curved along a length thereof.

In an embodiment, the engagement feature may include a longitudinal recess extending through a portion of the second one of the pair of arms and retaining tabs extending over a portion thereof to prevent disengagement of the needle therefrom once the needle has been received therein.

In an embodiment, the engagement feature may further include a curved surface extending along a distal portion of the longitudinal recess for guiding the needle thereinto.

In an embodiment, the device may further comprise a control member connected to the pair of arms for moving the pair of arms between the open configuration and the closed configuration.

In an embodiment, the device may further comprise a locking mechanism for locking the pair of arms in the closed configuration.

In an embodiment, the capsule may include a wedge feature along an interior surface thereof for locking the suture relative to the clip when the clip is in a locked configuration and a cutting feature for cutting a portion of the suture proximal of a wedged portion of the suture.

The present disclosure also relates to a method for treating a tissue opening, comprising inserting a clip to a target area within a patient body, the clip including a pair of arms movable between an open configuration in which distal ends of the pair of arms are separated from one another and a closed configuration in which distal ends of the pair of arms are drawn toward one another to grip tissue received therebetween, and a suture extending along a first one of the pair of arms and including a loop at a distal end thereof, the loop extending across an opening extending laterally through the first one of the pair of arms, positioning the pair of arms over a first portion of tissue along a tissue opening with the clip in the open configuration such that the first portion of tissue is received between the distal ends of the pair of arms, moving the clip toward the closed configuration so that a hook of suture grabbing element extending laterally from a second one of the pair of arms extends through the first portion of tissue and into the opening in the first one of the pair of arms to grab the loop extending across the opening, and moving the pair of arms to the open configuration such that the suture grabbing element is retracted from the first portion of tissue so that the suture is passed through the first portion of tissue.

In an embodiment, the method may further comprise, after moving the pair of arms to the open configuration with the suture passed through the first portion of tissue, positioning the pair of arms over a second portion of tissue along the tissue opening substantially opposing the first portion with the clip in the open configuration with the second portion of tissue is received between the distal ends of the pair of arms and moving the pair of anus to the closed configuration such that the pair of arms grip the second portion of tissue between distal ends of thereof.

In an embodiment, the method may further comprise pulling the suture proximally relative to the clip to draw the first portion of tissue toward the second portion of tissue.

In an embodiment, the method may further comprise locking the clip in the closed configuration.

In an embodiment, locking the clip may include locking the suture relative to the clip and cutting a portion of the suture extending proximally from the clip.

BRIEF DESCRIPTION

FIG. 26 shows yet another transparent side view of the device of FIG. 22;

FIG. 27 shows a perspective view of the device of FIG. 22;

DETAILED DESCRIPTION

Figure 1:
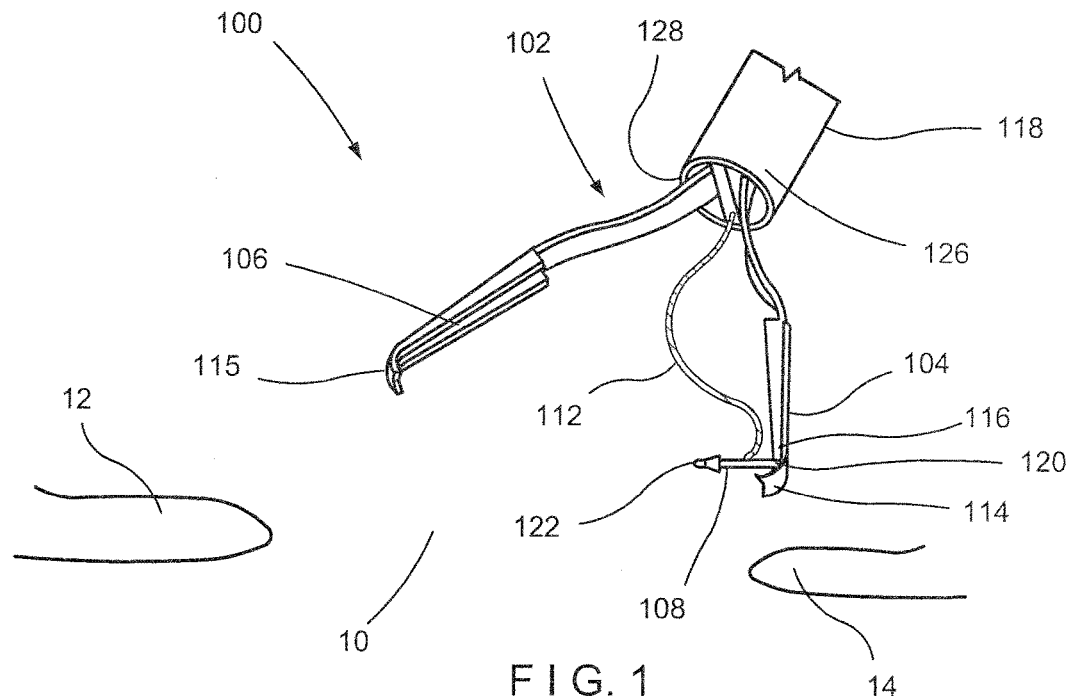
FIG. 1 shows a perspective view of a device according to an exemplary embodiment of the present disclosure, in a first configuration.

The present disclosure may be further understood with reference to the following description and the appended drawings, wherein like elements are referred to with the same reference numerals. The present disclosure relates to devices for tissue closure and, in particular, to an endoscopic tissue closure device. Exemplary embodiments of the present disclosure describe an endoscopic tissue closure device comprising a clip and a suture. The suture may be passed through a first portion of tissue along a tissue opening and the clip may be applied over a second portion of tissue along the tissue opening substantially opposing the first portion so that the first portion of tissue may be drawn toward the second portion by drawing the suture proximally relative to the clip. It should be noted that the terms "proximal" and "distal" as used herein, are intended to refer to a direction toward (proximal) and away from (distal) a user of the device.

As shown in FIGS. 1-10, a device 100 according to an exemplary embodiment of the present disclosure comprises a clip 102 including first and second arms 104, 106 movable between an open configuration and a closed configuration and a needle 108 extending laterally inward from the first arm 104 toward the second arm 106 to pass a suture 112 coupled to the needle 108 through a first portion of tissue 12 along a tissue opening 10. The device is inserted to a target spot within the body via, for example, a body lumen accessed via a naturally occurring bodily orifice. The device 100, however, may be inserted into the patient body in any of a number of different ways such as, for example, via a flexible endoscope, or through a rigid tube, etc. The clip 102 is movable between a closed configuration in which the first and second arms 104, 106, respectively, are drawn together in contact with one another and an open configuration in which distal ends 114, 115 of the first and second arms 104, 106, respectively, are separated from one another to permit a portion of tissue to be received therebetween. In the closed configuration, the distal ends 114, 115 of the arms 104, 106 are drawn toward one another to grip tissue received therebetween. The second arm 106 includes an opening 110 such as a slot or hole extending laterally therethrough. The opening 110 is sized and shaped to receive a portion of the needle 108 therein. The needle 108 is attached to the first arm 104 via a frangible link 116 such that when the arms 104, 106 are moved toward the closed configuration over the first portion of tissue 12, the needle 108 is passed through the first portion of tissue 12 into the opening 110 and locked therein so that when the clip 102 is moved once again to the open configuration, the frangible link 116 is broken leaving the needle 108 lodged in the second arm 110. As the clip 102 moves to the open configuration, the suture 112 is drawn through the first portion of tissue 12. The clip 102 is then opened and repositioned over a second portion of tissue 14 (e.g., a second portion of tissue on the periphery of the tissue opening 10 substantially opposite the first portion 12). Once the clip 102 has been repositioned as desired, the clip 102 is moved to the closed configuration to grip the second portion of tissue 14. The loop of suture 112 is then tightened to draw the first portion of tissue 12, through which the suture 112 is passed, toward the clip 102 until the first portion 12 is drawn against the second portion 14 closing the tissue opening 10.

The clip 102 may further include a capsule 118 in which the first and second arms 104, 106 are movably housed. The capsule 118 extends longitudinally from a proximal end 124 to a distal end 126 and includes a lumen 128 extending therethrough. Proximal ends of the first and second arms 104, 106 are slidably received within the lumen 128 so that the clip 102 may be moved between the open and the closed configurations. The first and second arms 104, 106 may be biased toward the open configuration such that when the first and second arms 104, 106 are moved distally out of the capsule 118, distal ends 114, 115 of the arms 104, 106 extend away from one another to the open configuration. When the first and second arms 104, 106 are drawn proximally into the capsule 118, however, the first and second arms 104, 106 are constrained via an interior surface 132 of the capsule 118 so that distal ends 114, 115 of the arms 104, 106 are drawn toward one another into the closed configuration. Distal ends 114, 115 may include gripping features such as, for example, teeth or tines extending laterally inward for gripping the tissue received therebetween. The clip 102 may be coupled to a proximal portion of the device 100, not shown, via a control member or other device which permits a user to move the clip 102 proximally and distally relative to the capsule 118 so that the clip 102 moves between the open and closed configurations.

In one embodiment, the capsule 118 may be coupled to a handle assembly (not shown), which remains outside of a patient body, via a flexible member to facilitate insertion of the clip 102 to a target area within the patient body through even tortuous paths of the body. The arms 104, 106 are moved with respect to the capsule 118 via the control member coupled to a proximal end of the arms 104, 106 and extending proximally through the flexible member to the handle assembly. The arms 104, 106 may be moved distally and proximally with respect to the capsule 118 between the open and closed configurations by moving the control member distally and proximally, respectively, via an actuator of the handle assembly. Once in the closed configuration, the control member may be drawn further proximally to lock the clip 102 in the closed configuration and disengage the clip 102 from the proximal portion of the device 100. For example, the clip 102 may be locked in the closed configuration by engagement between a portion of the clip 102 and a locking feature of the capsule 118 and disengaged from the proximal portion of the device by the separation of a frangible link substantially as described in U.S. Pat. No. 7,494,461 issued on Feb. 24, 2009 to Wells et al. In particular, when the control member of this embodiment is drawn proximally after a point of maximum proximal withdrawal of the clip 102 into the capsule 118, increased tension on the control member causes disengagement of the control member from the arms 104, 106, causing a bushing which connects the capsule 118 to the flexible member to become disengaged therefrom. The structural features of the clip 102, however, are not limited to those described in U.S. Pat. No. 7,494,461 and that the clip 102 may be deployed in the body in any of a number of ways via the further proximal motion of the control member with respect to the clip 102.

Figure 7:
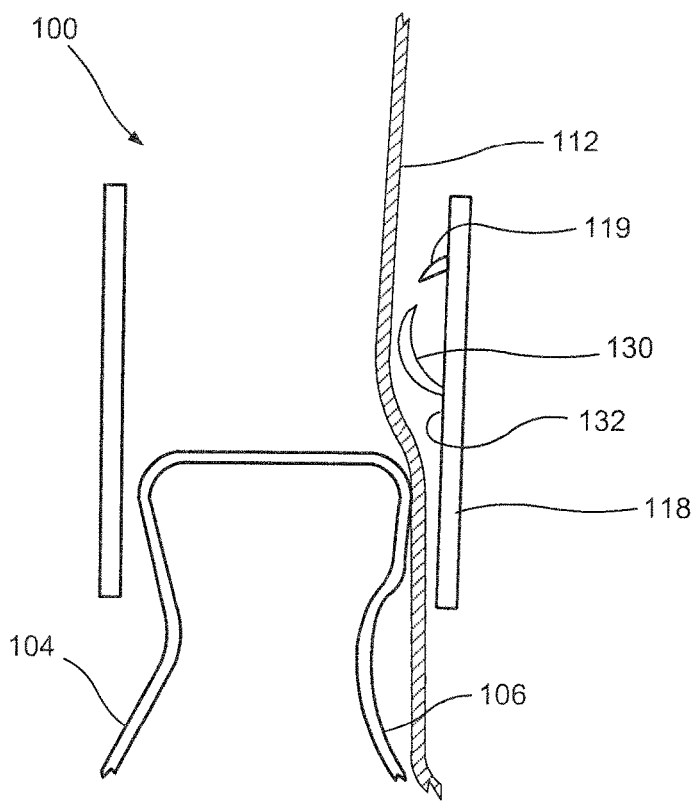
FIG. 7 shows a longitudinal cross-sectional view of a distal portion of the device of FIG. 1, in an unlocked configuration.
Figure 8:
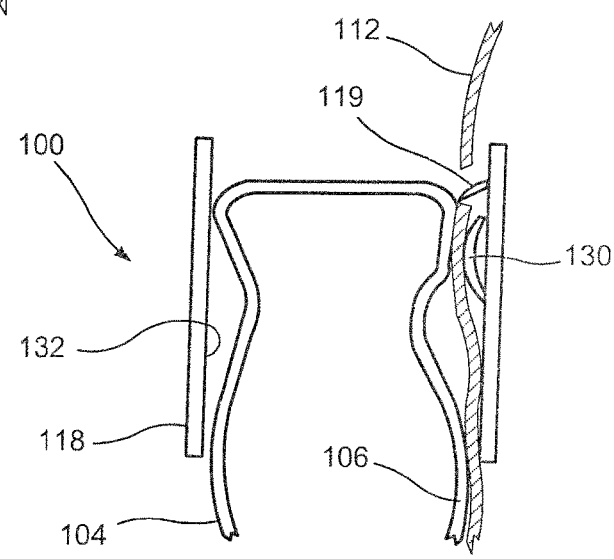
FIG. 8 shows a longitudinal cross-sectional view of the distal portion of the device of FIG. 1, in a locked configuration.

As shown in FIGS. 7-8, the clip 102 further includes a wedge feature 130 which wedges a portion of the suture 112 within the capsule 118. For example, the suture 112 may be wedged between one of the arms 104, 106 and the interior surface 132 of the capsule 118, when the clip 102 is in the locked configuration. A distal portion of the capsule 118 may be sized and shaped such that when the arms 104, 106 are drawn into the locked configuration, the arms 104, 106 and the capsule 118 form a friction fit with the portion of the suture 112 received therebetween locked therein. The capsule 118 may further include a cutting feature 119 along the interior surface 132 thereof for cutting a portion of the suture 112 extending proximally from the wedge. The cutting feature 119 of this embodiment is positioned on a portion of the capsule 118 proximal of the wedge feature. The cutting feature 119 may include, for example, a sharpened protrusion extending laterally inward and distally from the interior surface 132 of the capsule 118.

The needle 108 extends from a first end 120 attached to the first arm 104 via the frangible link 116 to a second end 122 extending laterally from the first arm 104 toward the second arm 106. The frangible link 116 may include, for example, a tight friction fit between the needle 108 and an opening in the first arm 104, an adhesive, weld, or solder joint designed to fail when subject to a force exceeding a predetermined threshold level. The frangible link 116 may include any of a variety of coupling mechanisms so long as the frangible link 116 fails when subject to a force exceeding the predetermined threshold level. Although this exemplary aspect is described and shown as including a frangible link 116 connecting the needle 108 to the first arm 104, the needle 108 may alternatively be connected to the first arm 104 via a releasable coupling. For example, the needle 108 may releasably engage a needle engaging feature in the first arm 104. The needle 108 may be released from this needle engaging feature via a force applied to the needle 108. The force may be, for example, a torsional force applied to the needle 108 by the second arm 106, which causes the needle 108 to rotate out of engagement with the needle engaging feature. Alternatively, the needle 108 may be actively released from the first arm 104, for example, by the user by means of a trigger mechanism of the like.

Figure 9:
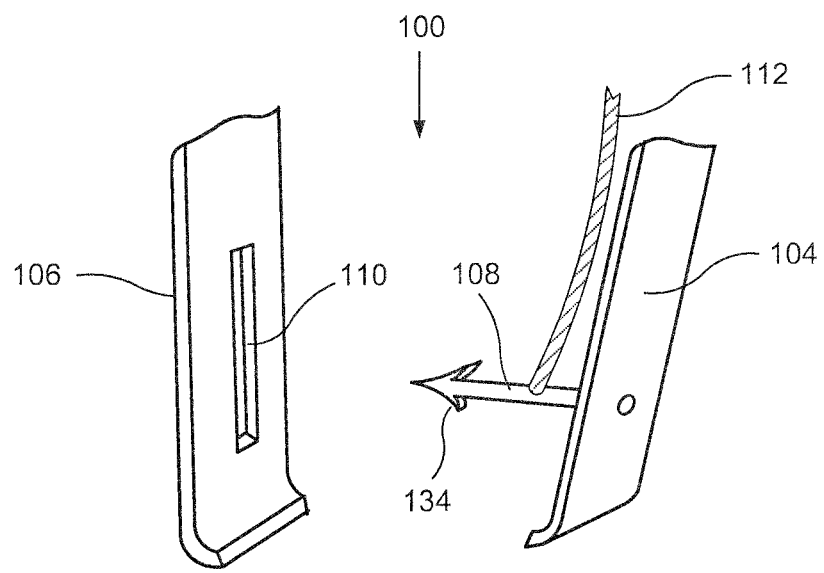
FIG. 9 shows a perspective view of arms of the clip of the device of FIG. 1, including a needle.
Figure 10:
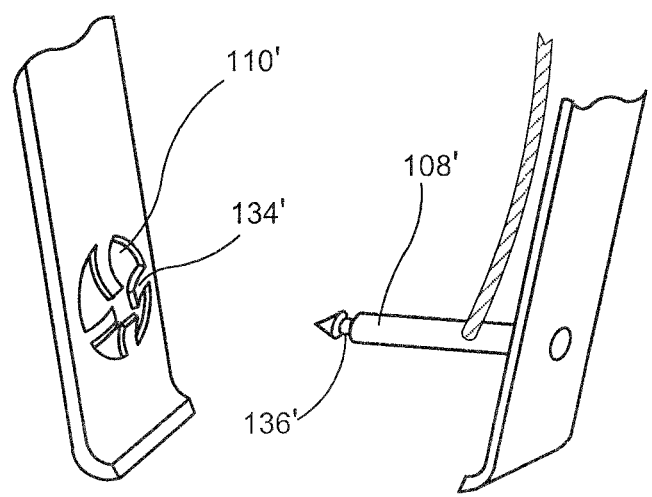
FIG. 10 shows a perspective view of arms of a clip according to an alternate embodiment of the device of FIG. 1.
Figure 11:
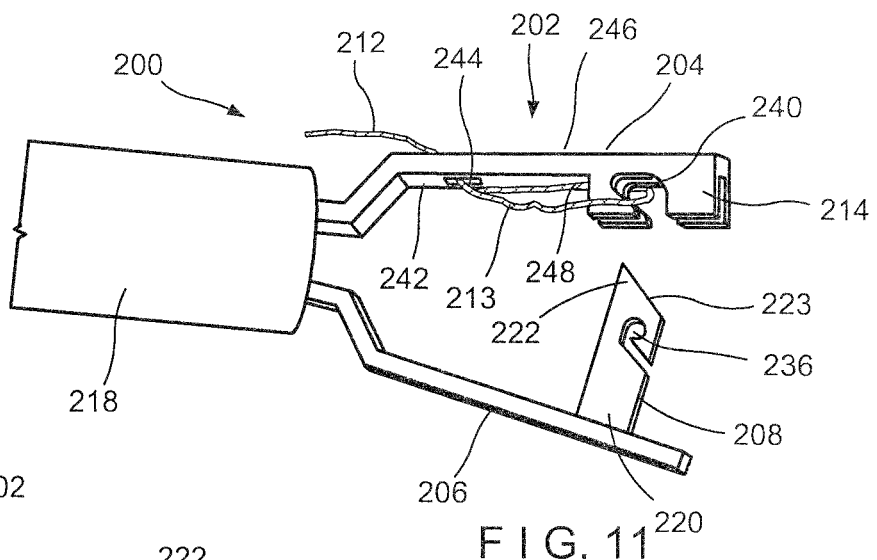
FIG. 11 shows a longitudinal side view of a device according to another exemplary embodiment in a first configuration.
Figure 12:
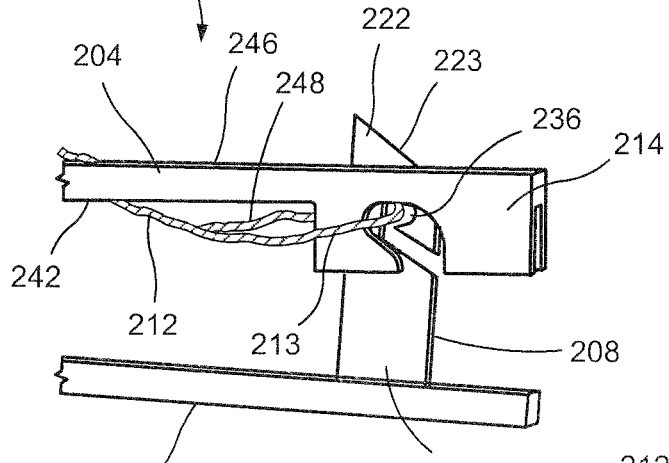
FIG. 12 shows a longitudinal side view of the device of FIG. 11, in a second configuration.
Figure 13:
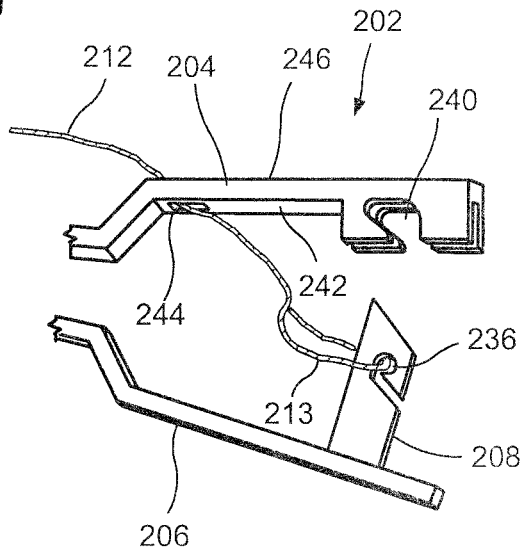
FIG. 13 shows a longitudinal side view of the device of FIG. 11, in a third configuration.
Figure 14:
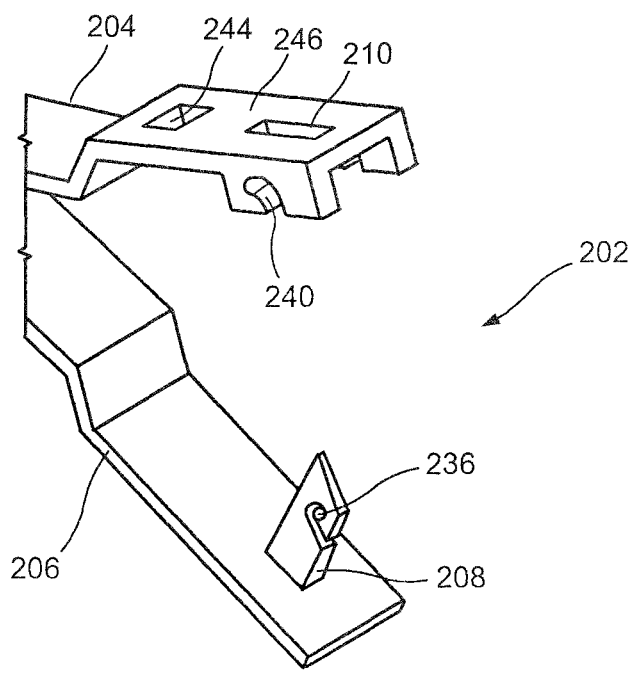
FIG. 14 shows a perspective view of a clip of the device of FIG. 11.
Figure 15:
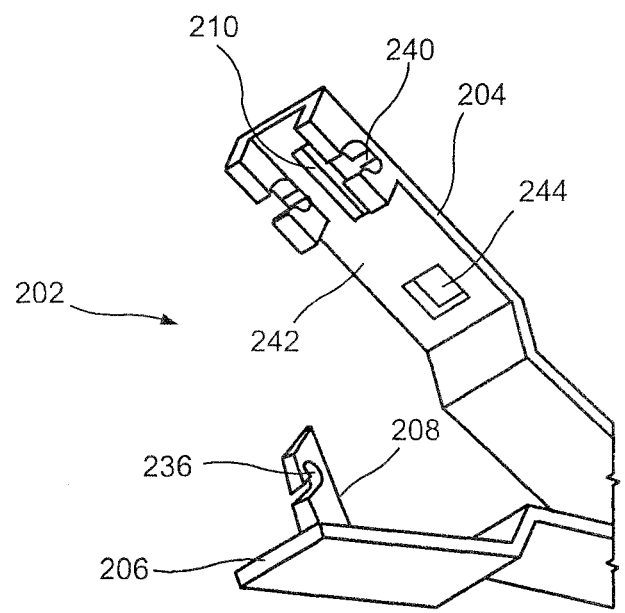
FIG. 15 shows another perspective view of the clip of the device of FIG. 11.

As shown in FIG. 9, a portion of the needle 108 includes barbs 134 therealong so that when the needle 108 is received within the opening 110 extending laterally through the second arm 106, the needle 108 engages the opening 110 so that the needle 108 is locked therewithin. In another embodiment, as shown in FIG. 10, the barb features 134' may be included in the opening 110' so that when the needle 108' is received therewithin, the opening 110' engages a groove 136' or other corresponding feature of the needle 108'. Although the exemplary embodiments describe barbs, the needle 108 and the opening 110 of the second arm 106 may include any of a variety of corresponding locking features so long as the needle 108 is locked within the opening 110 when received therein.

The suture 112 extends from a distal end 120 connected to the needle 108 to a proximal end (not shown) extending proximally through the capsule 118 and the proximal portion of the device 100 to the handle assembly. The suture 112 is slidably received within the capsule 118 so that the suture 112 may be slackened and tightened, as desired. The proximal end of the suture 112 may be coupled to an actuating feature of the handle assembly so that the suture 112 may be tightened via the actuating feature on the handle assembly. Alternatively, the proximal end of the suture 112 may extend from the handle assembly so that the user may draw the proximal end proximally with respect to the device 100 to tighten the suture 112. The distal end 120 of the suture 112 should be connected to a portion of the needle 108 between the locking feature (e.g., barbs) of the needle 108 and the first end 120 so that locking the needle 108 within the opening 110 does not interfere with the slackening and tightening of the suture 112.

According to a method using the device 100, the clip 102, with the needle 108 connected to the first arm 104, is inserted to a target area in the patient body through, for example, a working channel of an endoscope. The clip 102 may be inserted through the working channel in an insertion configuration with the handle assembly remaining outside the patient's body. In this insertion configuration, the first and second arms 104, 106 are drawn toward one another with the needle 108 connected to the first arm 104. The needle 108, however, is prevented from engaging the second arm 106. Once the clip 102 has reached the tissue opening 10 to be closed, the clip 102 is moved to the open configuration by moving the clip arms 104, 106 distally with respect to the capsule 118 so that the arms 104, 106 are permitted to revert to their biased open position, as shown in FIG. 1. In the open configuration, the arms 104, 106 are positioned so that the first portion of tissue 12 may be received therebetween.

Figure 2:
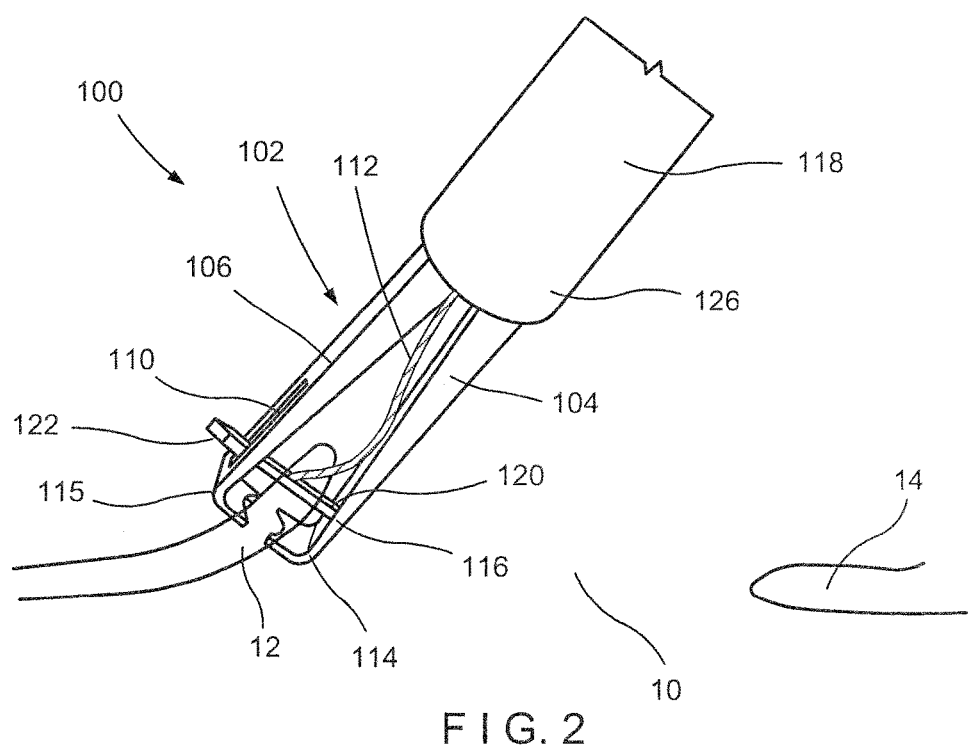
FIG. 2 shows another perspective view of the device of FIG. 1, a clip of the device gripping a first portion of tissue of a tissue opening.
Figure 3:
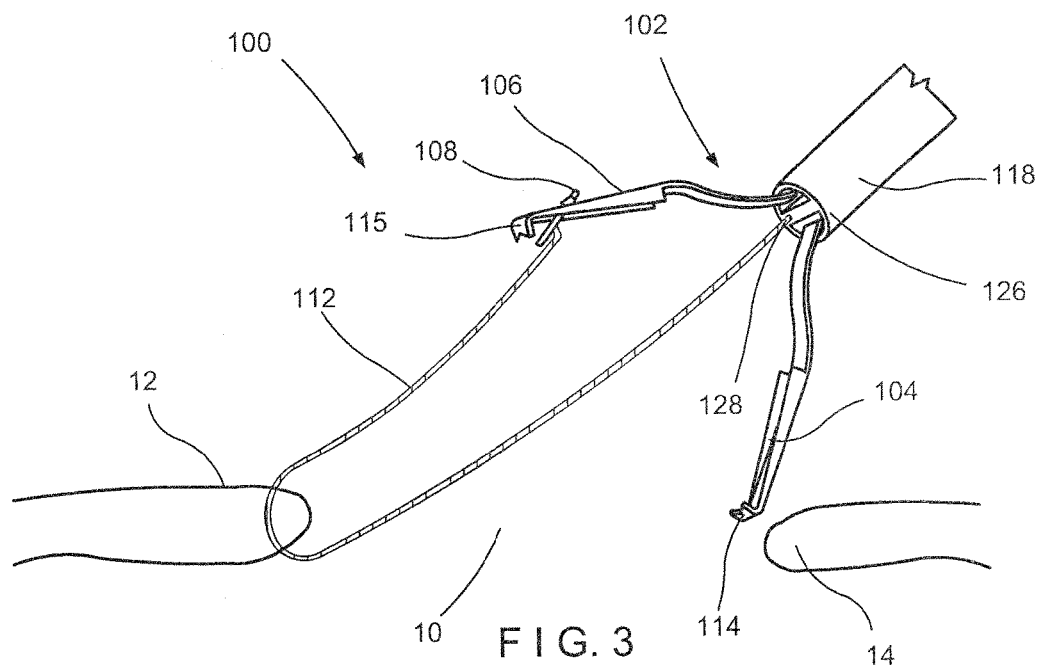
FIG. 3 shows another perspective view of the device of FIG. 1, in a second configuration.

Once positioned, as desired, the clip 102 is moved to the closed configuration to grip the first portion of tissue 12 between arms 104, 106 by drawing the clip arms 104, 106 into the capsule 118 so that the arms 104, 106 are constrained thereby. As the clip 102 is moved to the closed configuration, as shown in FIG. 2, the needle 108 extending laterally from the first arm 104 passes through the first portion of tissue 12 and engages the opening 110 of the second arm 106. Prior to the needle 108 engaging the opening 110 of the second arm 106, however, the arms 104, 106 may be moved between the open and closed positions to adjust the placement of the arms 104, 106 over tissue, as desired. This movement may be controlled by a user interface having incremental closing positions controlled to prevent premature engagement of the needle 108 or via tactile features that have threshold forces to actuate between states. Once the needle 108 has engaged the opening 110 of the second arm 106, however, the clip 102 is moved to the open configuration so that distal ends 114, 115 of the arms 104, 106 are once again separated from one another. Since the needle 108 is locked within the opening 110 of the second arm 106, the separation of the distal ends 114, 115 causes the frangible link 116 connecting the first end 120 of the needle 108 to the first arm 104 to break. The needle 108, however, remains locked in the opening 110 so that the suture 112 is passed through the first portion of tissue 12. As the clip 102 is moved to the open configuration, the clip 102 is also moved proximally relative to the first portion of the tissue 12, causing the clip 102 to be moved proximally with respect to the suture 112, such that a slack in the suture 112 is formed, as shown in FIG. 3.

Figure 4:
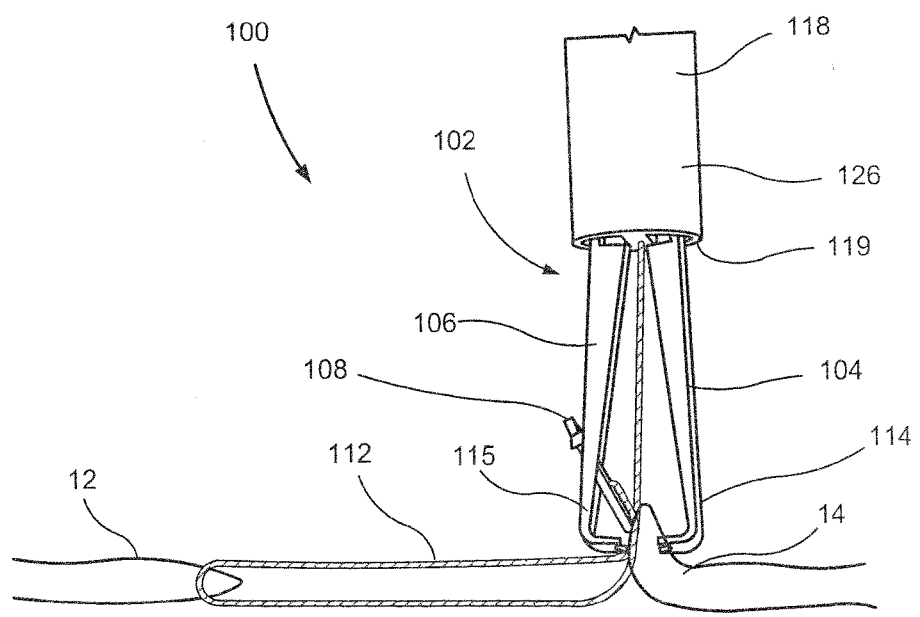
FIG. 4 shows a side view of the device of FIG. 1, the clip gripping a second portion of tissue of the tissue opening.
Figure 5:
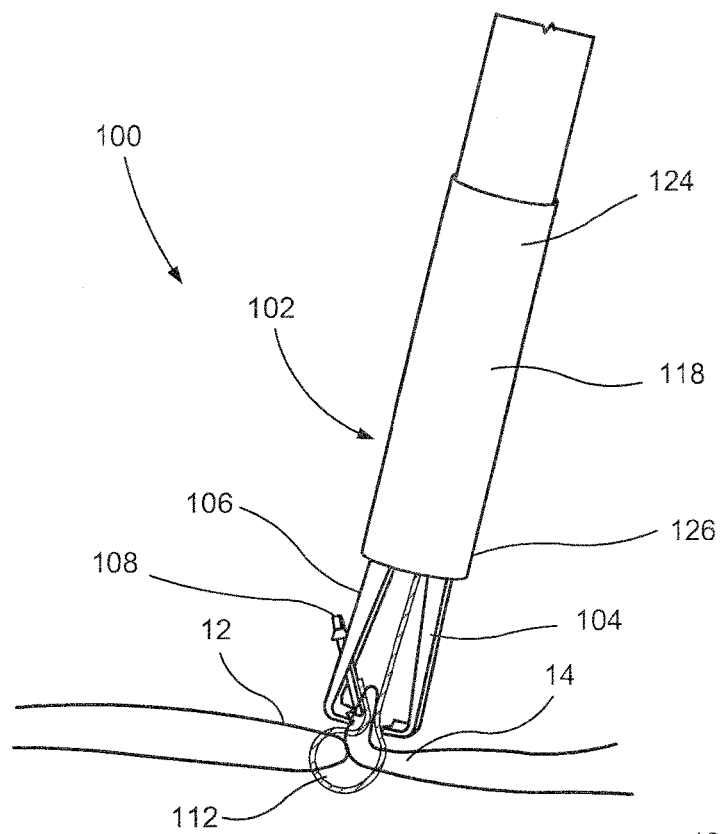
FIG. 5 shows a perspective view of the device of FIG. 1, with the first and second tissue portions drawn toward one another.

The clip 102 is then moved to the second portion of tissue 14 substantially opposing the first portion 12 and positioned thereover such that the second portion 14 is received between the arms 104, 106. As shown in FIG. 4, once the clip 102 has been positioned over the second portion, as desired, the clip 102 is moved to the closed configuration to grip the second portion of tissue 14 between the arms 104, 106. The suture 112 is then drawn proximally with respect to the clip 102, drawing the first portion of tissue 12 toward the second portion of tissue 14 to close the tissue opening 10, as shown in FIG. 5. Although the exemplary embodiments show and describe the clip 102 as being moved to the locked configuration once the clip 102 has been clipped over the second portion of tissue 14 and the first portion of the tissue 12 has been drawn theretoward via the suture 112, the clip 102 may be repositioned prior to locking, if so desired. For example, clip arms 104, 106 may be repositioned to get a better grasp of the second portion of tissue 14.

Figure 6:
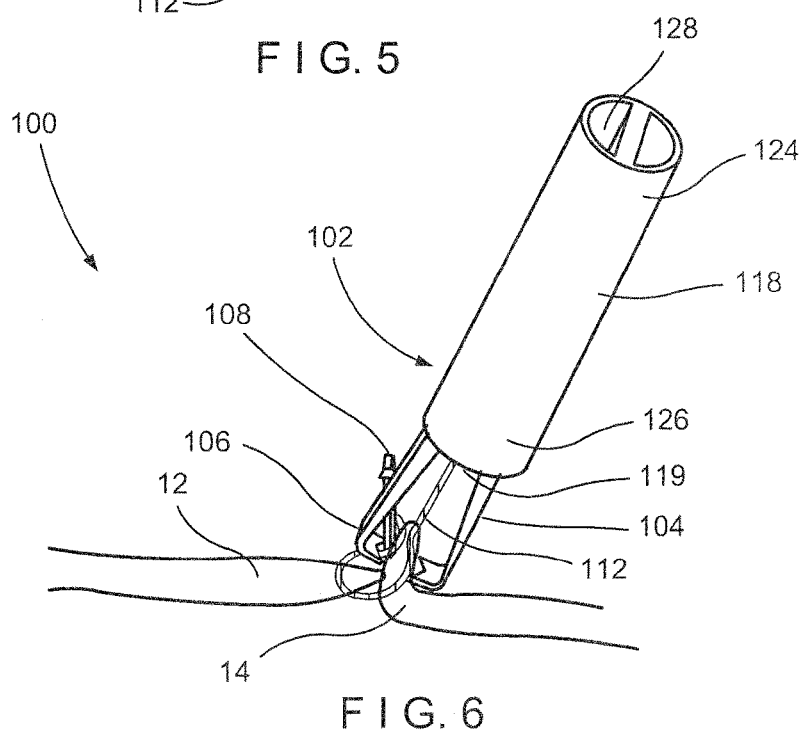
FIG. 6 shows another perspective view of the device of FIG. 1, in a locked configuration.

In another example, the clip 102 may be repositioned to extend over both the first and second portions of tissue 12, 14, once the first and second portions of tissue 12, 14 have been drawn toward one another, so that the clip 102 grips both portions of tissue 12, 14. Once the tissue opening 10 is closed, as desired, the clip 102 may be locked, as shown in FIG. 6, by drawing the control member further proximally with respect to the clip 102. As described above, moving the clip 102 to the locked configuration will also cause a portion of the suture 112 to become wedged between one of the clip arms 104, 106 and the interior of the capsule 118. Upon wedging of the suture 112 between the clip arms 104, 106, a portion of the suture extending proximally of the wedge is cut therefrom via the cutting feature along the interior of the capsule 118. The proximal portion of the device 100 is then removed from the body such that only the clip 102, the needle 108, and a distal portion of the suture 112 remain within the body to hold the tissue opening 10 in the closed position.

As shown in FIGS. 11 to 15, a device 200 according to another exemplary embodiment of is substantially similar to the device 100 described above, comprising a clip 202 including first and second arms 204, 206 movable between an open configuration and a closed configuration via, for example, a capsule 218 slid longitudinally thereover as described above in regard to the device 100. Rather than a needle for passing a suture 212 from the first arm 204 to the second arm 206, however, the suture 212 extends along a portion of the first arm 204 so that a suture grabbing element 208 extending laterally inward from the second arm 206 hooks a portion of the suture 212 as the clip 202 is moved toward the closed configuration. In use, the clip 202 is positioned in the open configuration over tissue (e.g., along a first side of a tissue opening) so that a first portion of tissue along the first side is received between the first and second arms 204, 206. The clip 202 may then be moved toward the closed configuration so that the suture grabbing element 208 pierces the portion of tissue received between the first and second arms 204, 206 as the suture grabbing element 208 is moved toward the first arm 204. A hook feature 236 at an end 222 of the suture grabbing element 208 interfaces with a portion of the first arm 204 to hook a loop 213 of the suture 212 extending along the first arm 204. The clip 202 is once again moved to the open configuration so that the suture grabbing element 208, with the suture 212 hooked thereto, is removed from the first portion of tissue, passing the suture 212 through the first portion of tissue in the process. Similarly to the device 100, after passing the suture 212 through the first portion of tissue, the clip 202 may then be positioned over a second portion of tissue (e.g., along a second side of the tissue opening) so that the second portion of tissue is received between the first and second arms 204, 206. Once the clip 202 has been repositioned, as desired, the clip 202 is moved to the closed configuration to grip the second portion of tissue. The suture 212 is then tensioned to draw the first portion of tissue, through which the suture 212 has been passed, toward the second portion of tissue, thereby closing the tissue opening.

The clip 202 is substantially similar to the clip 102, described above except as specifically noted. In particular, the clip 202 may, for example, be biased toward the open configuration so that, when the first and second arms 204, 206 are moved distally out of the capsule 218, the first and second arms 204, 206 extend away from one another toward the open configuration. When the first and second arms 204, 206 are drawn proximally into the capsule 218, however, the first and second arms 204, 206 are constrained via an interior surface of the capsule 218 toward the closed configuration. In one embodiment, the capsule 218 may be coupled to a handle assembly, which remains outside of a patient body, via a flexible member to facilitate insertion of the clip 202 to a target within the patient body. The clip 202 may be moved between the open and closed configuration by moving a control member coupled to a proximal end of the first and second arms 204, 206 via an actuator of the handle assembly, as described above in regard to the clip 102. Once in the closed configuration, the control member is drawn further proximally to lock the clip 202 in the closed configuration and disengage the clip 202 from a proximal portion of the device 200, as described with respect to the device 100.

The first arm 204 of the clip 202, however, includes a notch 240 along an interior surface 242 of the first arm 204 at a distal end 214 thereof. The first arm 204 also includes a slot 210 extending laterally through the distal end 214 thereof in communication with the notch 240. In other words, the slot 210 extends through the first arm 204 and through the notch 240 so that, when a loop 213 of the suture 212 is hooked on the notch 240, a portion of the loop 213 extends across the slot 210. Thus, the suture grabbing element 208 passes through the slot 210, between opposing sides of the notch 240, to hook a portion of the loop 213. The first arm 204 may further include an opening 244 extending laterally therethrough, the opening 244 separated from the slot 210 by a small distance.

In this embodiment, a length of the suture 212 extends from a proximal end coupled to an actuating feature of the handle assembly through the flexible member and the capsule 218 along an exterior surface 246 of the first arm 204. Once the suture 212 reaches the opening 244, however, the suture 212 is fed through the opening 244 so that a remaining distal length of the suture 212 extends along the interior surface 242 of the first arm 204 to be hooked via the loop 213 at its distal end 248. The loop 213 of the suture 212 is hooked by opposing sides of the notch 240 so that a portion of the loop 213 extends across the slot 210. Thus, when the suture grabbing element 208 is passed through the slot 210, the suture grabbing element 208 passes through the loop 213 to grab a portion thereof, hooking the loop 213.

The second arm 206 is substantially similar to the second arm 106 of the clip 102 except as specifically noted below. In contrast to the clip 102, the second arm 206 includes the suture grabbing element 208 extending laterally from a first end 220 connected to the second arm 206 to a second end 222 extending toward the first arm 204. The second end 222 includes a hooked recess 236 therein. The second end 222 may also include an angled surface 223 configured so that, as the suture grabbing element 208 is inserted through the slot 210, the loop 213 of the suture 212 is guided along the angled surface 223 until the loop 213 reaches the hooked recess 236 and is received therein. The suture grabbing element 208 is positioned along the second arm 206 so that, when the clip 202 is moved toward the closed configuration, at least a portion of the suture grabbing element 208 is received within the slot 210 so that the hooked recess 236 hooks the loop 213 of the suture 212 hooked via the notch 240. The second end 222 may also include an angled surface 223 configured so that, as the suture grabbing element 208 is inserted through the slot 210, the loop 213 of the suture 212 is guided along the angled surface 223 until the loop 213 reaches the hooked recess 236 and is received therein. The hooked recess 236 is shaped so that, upon hooking the loop 213, the suture 212 is prevented from being unhooked from the hooked recess 236.

The device 200 may be used in a manner substantially similar to the device 100. Rather than passing the suture 212 through the first portion of tissue via a needle, however, the suture is passed through the first portion of tissue via the suture grabbing element 218. In particular, the clip 202 is positioned along the first portion of tissue (e.g., along a first side of a tissue opening) in the open configuration with the first portion of tissue received between the first and second arms 204, 206. The clip 202 is then moved toward the closed configuration so that the suture grabbing element 208 extends through the first portion of tissue, between opposing sides of the notch 240 into the slot 210 to hook the loop 213 of the suture 212 via the hooked recess 236. Once the loop 213 has been hooked via the hooked recess 236, the clip 202 is moved toward the open configuration so that the suture grabbing element 208, with the suture 212 hooked therethrough, is removed from the first portion of tissue. Removal of the suture grabbing element 208 from the first portion of tissue draws the suture 212 through the first portion of tissue so that the distal end 248 of the suture 212 is now attached to the second arm 206.

The clip 202 is then be moved toward a second portion of tissue (e.g., along a second side of the tissue opening) until the second portion of tissue is received between the first and second arms 204, 206 in the open configuration. Opening of the first and second arms 204, 206 and moving the clip 202 toward the second side of the tissue opening creates slack in the suture 212 so that a length of the suture 212 extends across the tissue opening. The clip 202 may then be moved toward the closed configuration to grip the second portion of tissue between the first and second arms 204, 206. Once the second portion of tissue has been gripped, as desired, the suture 212 is tensioned by drawing the suture 212 proximally relative to the clip 202. Tensioning the suture 212 draws the first portion of tissue, through which the suture 212 is passed, toward the second portion of tissue to close the tissue opening. Once the tissue opening is closed, the clip 202 may be locked by drawing the clip arms 204, 206 further proximally into the clip 202. As described above in regard to the device 100, a wedge feature along an interior of the capsule 218 may wedge the suture 212 between the first arm 204 and the capsule 218 while a cutting feature cuts a portion of the suture 212 extending proximally from the wedge. Similarly to the device 100, locking the clip 202 in the closed configuration deploys the clip 202—and a distal portion of the suture 212—in the body.

Figure 16:
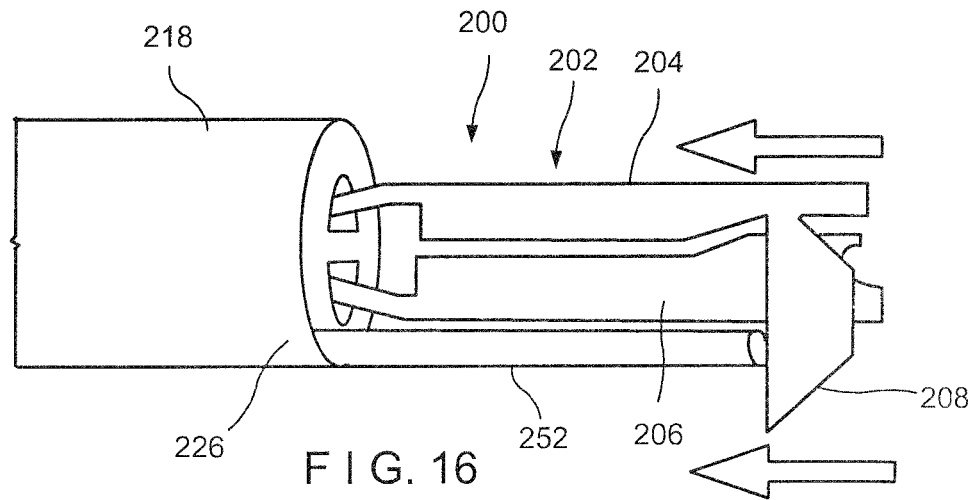
FIG. 16 shows a longitudinal side view of the device of FIG. 11, according to a further embodiment.

According to a further embodiment, as shown in FIG. 16, the device 200 further comprises a longitudinal extension 252 extending from a distal end 226 of the capsule 218. The longitudinal extension 252 is sized and configured to interface with the suture grabbing element 208, as the clip 202 is moved toward the locked configuration. In particular, as the clip 202 is moved toward the locked configuration, the suture grabbing element 208 comes into contact with the longitudinal extension 252. Further proximal motion of the first and second arms 204, 206 relative to the capsule 218 forces the suture grabbing element 208 to bend toward the first arm 204, reducing the risk of the suture grabbing element 208 causing damage to surrounding tissue upon deployment of the clip 202.

Figure 17:
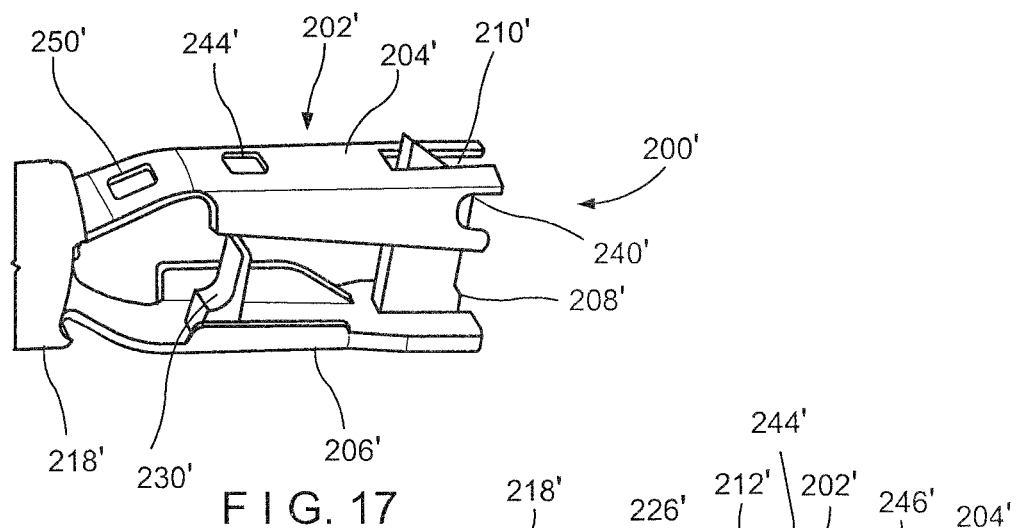
FIG. 17 shows a perspective view of a device according to an alternate embodiment.
Figure 18:
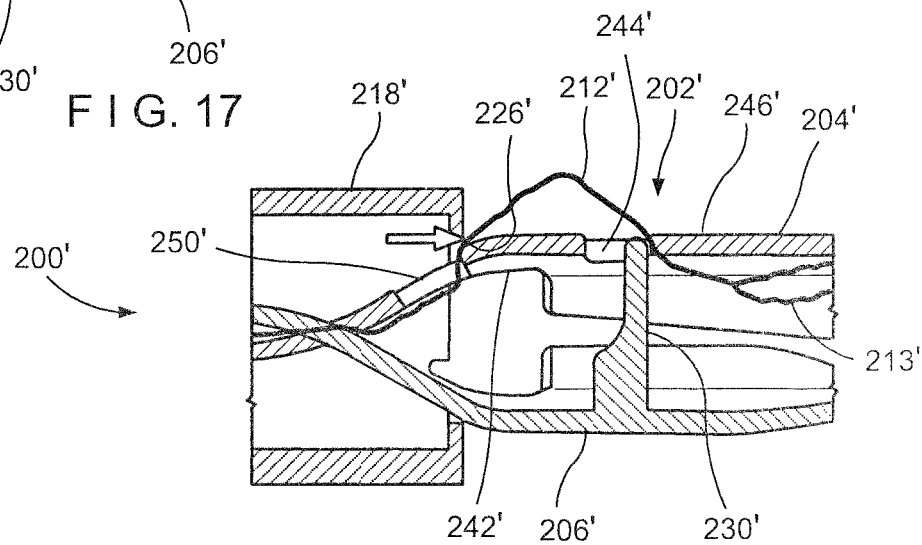
FIG. 18 shows a longitudinal cross-sectional view of the device of FIG. 17.

In another exemplary embodiment, as shown in FIGS. 17 and 18, a device 200' is substantially similar to the device 200 described above except as described below. Rather than the wedge and cutting features of a capsule, as described above, however, first and second arms 204', 206' of a clip 202' of the device 200' include features for wedging and/or cutting a suture 212'. The clip 202' is substantially similar to the clip 202 described above except as distinguished below. The first arm 204', however, in addition to a notch 240', a slot 210' and a first opening 244', includes a second opening 250' extending laterally therethrough, proximally of the first opening 244'. The suture 212' may extend from a proximal end, through the flexible member and capsule 218' between the first and second arms 204', 206', until the suture 212 reaches the second opening 250'. The suture 212' may be passed from an interior 242' of the first arm 204' through the second opening 250' to an exterior 246' of the first arm 204' so that a portion of a length of the suture 212' extends along the exterior 246' of the first arm 204' between the second and first openings 250', 244'. Upon reaching the first opening 244', the suture 212' is passed through the first opening 244' so that a distal loop 213' of the suture 212' may be hooked onto the notch 240'.

The second arm 206' includes, in addition to a suture receiving element 208', a wedge element 230' extending laterally therefrom toward the first arm 204' so that, when the clip 202' is moved toward a locked configuration, the wedge element 230' extends through the first opening 244' against an edge thereof to wedge or pinch the suture 212' between the wedge element 230 and the edge of the first opening 244'. Upon being moved to the locked configuration, a distal edge 226' of a capsule 218' cuts a portion of the suture 212' extending between the first and second openings 244', 250'. The device 200' may be used in manner substantially similar to the device 200, described above except as distinguished below.

Although the device 200' is described as including a wedging of the suture 212' via the wedge element 230' and cutting of the suture 212' between the first and second openings 244', 250' via the distal edge 226' of the capsule 218', in an alternative embodiment, the suture 212' may be cut in a manner substantially similar to the devices 100, 200 described above. While the suture 212' may be wedged between an edge of the first opening 244' and the wedge element 230', the suture 212' may be cut via a cutting feature along an interior of the capsule 218'.

Figure 19:
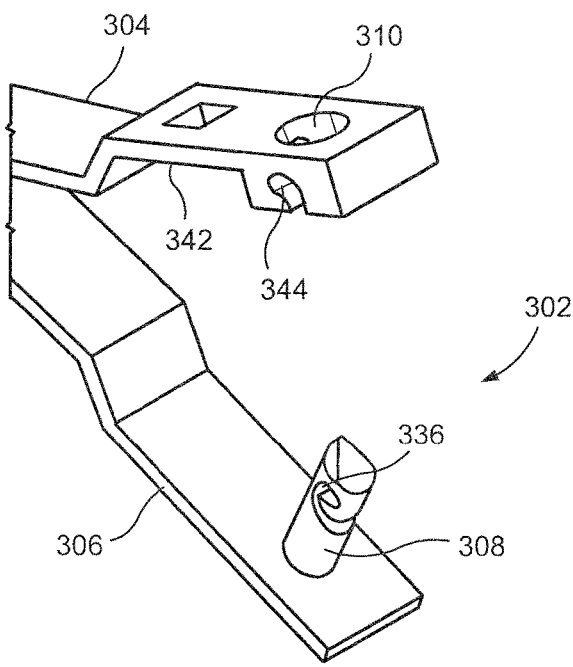
FIG. 19 shows a perspective view of a clip according to another exemplary embodiment.

A suture grabbing element and a slot or opening across which a loop of a suture extends may be formed in any of a variety of shapes and configurations, so long as a hook feature of the suture grabbing element is able to pass through the slot or opening to hook the loop of the suture. For example, in one embodiment, as shown in FIG. 19, a clip 302 may be substantially similar to the clips 202, 202' described above. Rather than a substantially planar suture grabbing element received through a correspondingly shaped slot, a first arm 304 of the clip 302 may include a substantially circular opening 310 extending therein, through a notch extending along an interior surface 342 of the first arm 304. A suture grabbing element 308 extending laterally from a second arm 306 of the clip 302 may be configured as a needle or wire including a hooked recess 336 extending therein.

Figure 20:
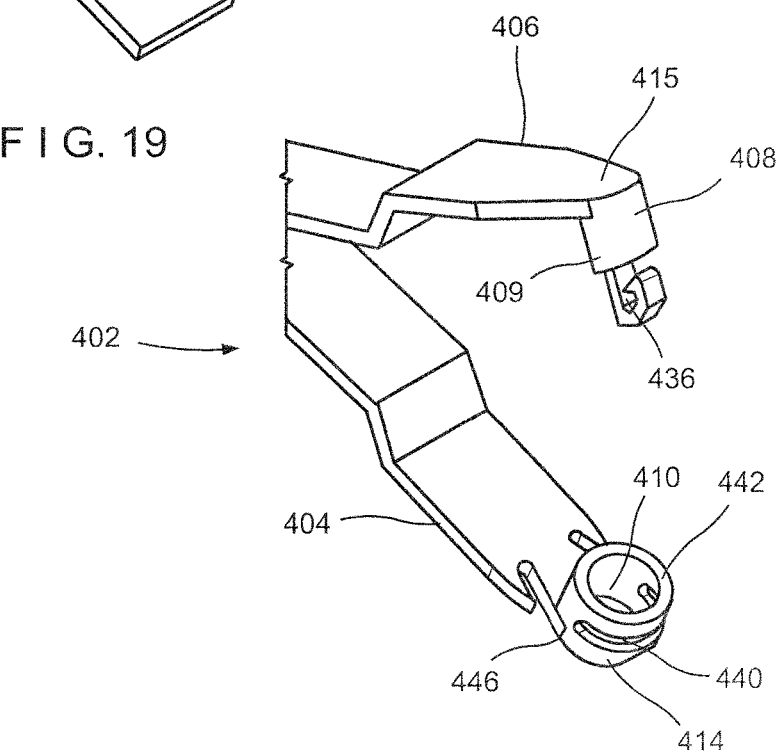
FIG. 20 shows a perspective view of a clip according to yet another exemplary embodiment.

In another example, as shown in FIG. 20, a clip 402 may be substantially similar to the clips 202, 302 describe above, comprising first and second arms 404, 406. The first arm 404, however, includes a substantially circular opening 410 extending laterally through a distal end 414 thereof. The notch, however, is configured as a slot 440 extending proximally into the first arm 404 from a distal edge 414 thereof, between an interior 442 and exterior surface 446 of the first arm 404. Thus, when a suture loop is inserted into the slot 440, a portion of the loop extends across the opening 410. A suture grabbing element 408 may be configured as a circular protrusion 409 extending laterally from a distal end 415 of the second arm 408 and including a hook 436 extending therefrom.

Figure 21:
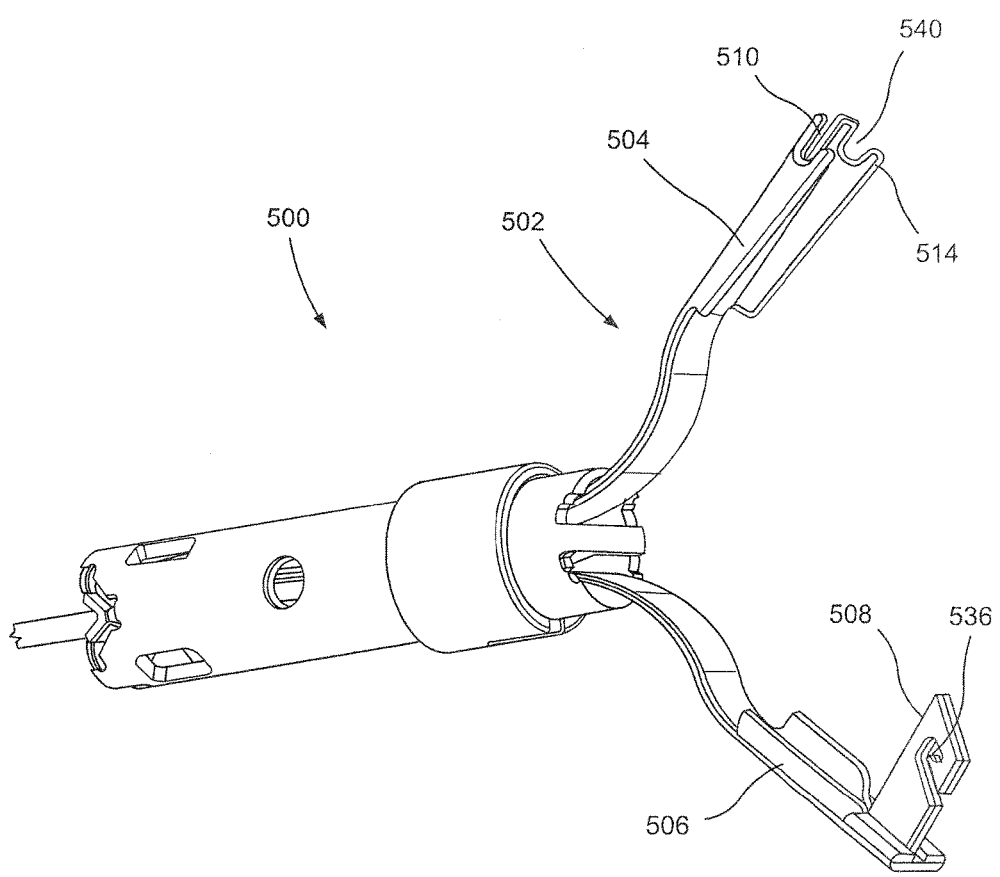
FIG. 21 shows a perspective view of another exemplary embodiment.

In an alternate embodiment, as shown in FIG. 21, a device 500 comprises a clip 502 substantially similar to the clips 202, 302, 402 described above except as distinguished below. The clip 502 includes first and second arms 504, 506 and the first arm 504, however, includes a slotted opening 510 open to a distal end 514 thereof. A notch is configured as a second slot 540 extending proximally from and open to the distal end 514 so that, when a suture loop is received within the second slot 540, a portion of the loop extends across the slotted opening 510. The second arm 506 includes a suture grabbing element 506 extending laterally therefrom, toward the first arm 508. The suture grabbing element 508 may be substantially similar to the suture grabbing element 208 described above in regard to the device 200, including a hooking recess 538 extending therein so that, when the first and second arms 504, 506 are drawn toward one another, the suture grabbing element 508 extends through the slotted opening 510 to hook the portion of the suture extending thereacross.

As shown in FIGS. 22-27, a device 600 according to another exemplary embodiment may be substantially similar to the device 100 described above except as noted below, comprising a clip 602 including first and second arms 604, 606 movable relative to one another between an open configuration and a closed configuration and a needle 608 releasably coupled to the first arm 604 to pass a suture 612 connected to the needle 608 through a first portion of tissue along a first side of tissue opening. Although not shown, the clip 602 may be moved between the open and closed configurations via a capsule in a manner substantially similar to that described above for the capsule 118. Similarly to the device 100, when the clip 602 is moved toward the closed configuration over the first portion of tissue, the needle 608 is passed through the first portion of tissue to engage with an engaging feature 610 of the second arm 606 so that, when the clip 602 is moved once again to the open configuration, the needle 608 is released from the first arm 604, leaving the needle 608 engaged with the second arm 606. As the clip 602 moves to the open configuration, the suture 612 is drawn through the first portion of tissue. The clip 602 is then opened and repositioned over a second portion of tissue (e.g., along a second side of a tissue opening). Once the clip 602 has been repositioned as desired, the clip 602 is moved to the closed configuration to grip the second portion of tissue between the first and second arms 604, 602. The suture 612 is then tensioned to draw the first portion of tissue, through which the suture 612 has been passed, toward the second portion of tissue, over which the clip 602 is clipped, until the first portion of tissue is drawn against the second portion of tissue, closing the tissue opening.

Figure 22:
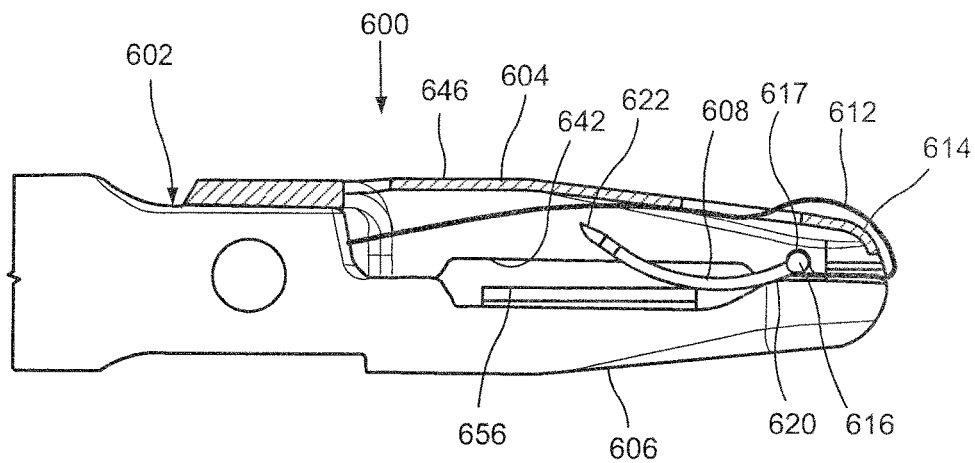
FIG. 22 shows a partially transparent side view of a device according to another exemplary embodiment in a preloaded insertion configuration.
Figure 23:
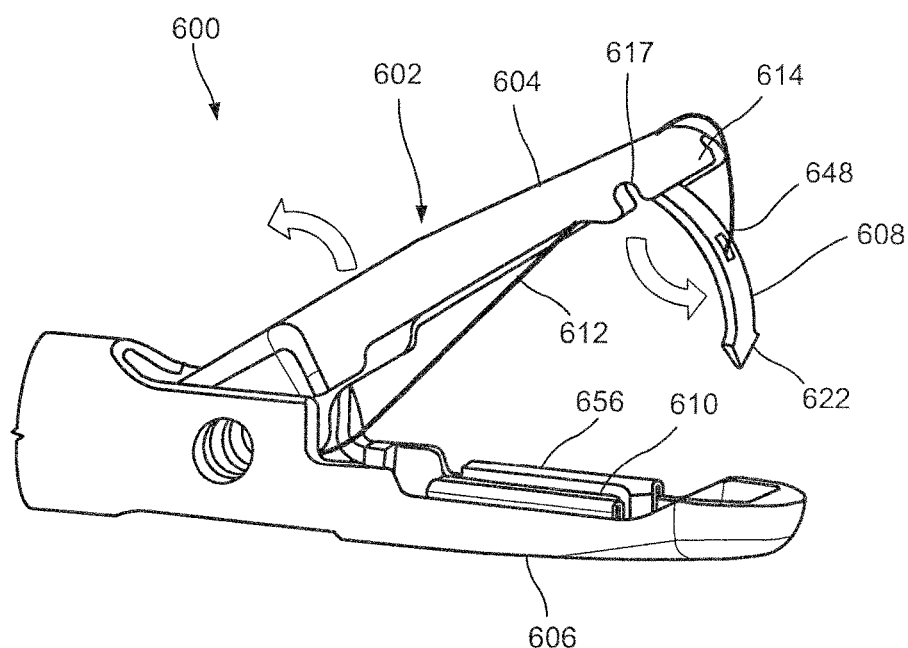
FIG. 23 shows a perspective view of the device of FIG. 22, in a firing position.

In this embodiment, the second arm 606 may be substantially rigid while the first arm 604 is pivotally coupled thereto to be moved relative to the second arm 606 between the open and the closed configurations. The needle 608 is preloaded onto the first arm 604 and is coupled thereto via a releasable hinge 616 at an end thereof. The hinge 616 of the needle 608 is received within a correspondingly shaped recess 617 along an interior 642 of the first arm 604 via a snap fit which permits the needle 608 to pivot about the hinge 616 when received within the recess 617. The needle 606 may be curved along a length thereof and movable between a preloaded insertion configuration, as shown in FIG. 22, and a firing position, as shown in FIG. 23. In particular, when the hinge 616 is engaged with the recess 617, the needle 608 pivots about the hinge 616 at a first end 620 of the needle 608 so that a second end 622 of the needle 608 may be moved from the preloaded insertion configuration, in which the second end 622 extends toward the first arm 604, to a firing position in which the second end 622 extends toward the second arm 606. Although the needle 608 is described and shown as being coupled to the first arm 604 via a hinge 616, the needle 608 may be releasably coupled to the first arm 604 in any of a variety of ways so long as the needle 608 is pivotal relative thereto, as described above.

The second arm 606 includes the engaging feature 610 which may be configured as a longitudinal recess 654 extending through a portion of the second arm 606 along with restraining tabs 656 extending over a portion of the longitudinal recess 654 to prevent the needle 608 from being disengaged from the second arm 606 once the needle 608 is received within the longitudinal recess 654. The longitudinal recess 654 is sized and shaped to receive the needle 608 and may include a curved surface 658 for guiding the needle 608 thereinto as the clip 602 is moved toward the closed configuration. Once the needle 608 has been received therein, the needle 608 is prevented from being disengaged therefrom via the restraining tabs 656.

Similarly to the devices 100, 200, the suture 612 may extend from a proximal end coupled to a handle assembly of the device 600, through a flexible member and capsule coupled to the clip 602 to a distal end 648 connected to the needle 608. Similarly to the clip 202, the first arm 604 may include an opening 644 through which the suture 612 may extend from the interior 642 of the first arm 604 to an exterior 646 of the first arm 604. In the preloaded insertion configuration, the suture 612 extends along the exterior 646 about a distal end 614 of the first arm to the distal end 648 connected to the needle 608, which is pivotally coupled to the interior 642 of the first arm 604 via the hinge 616.

Figure 24:
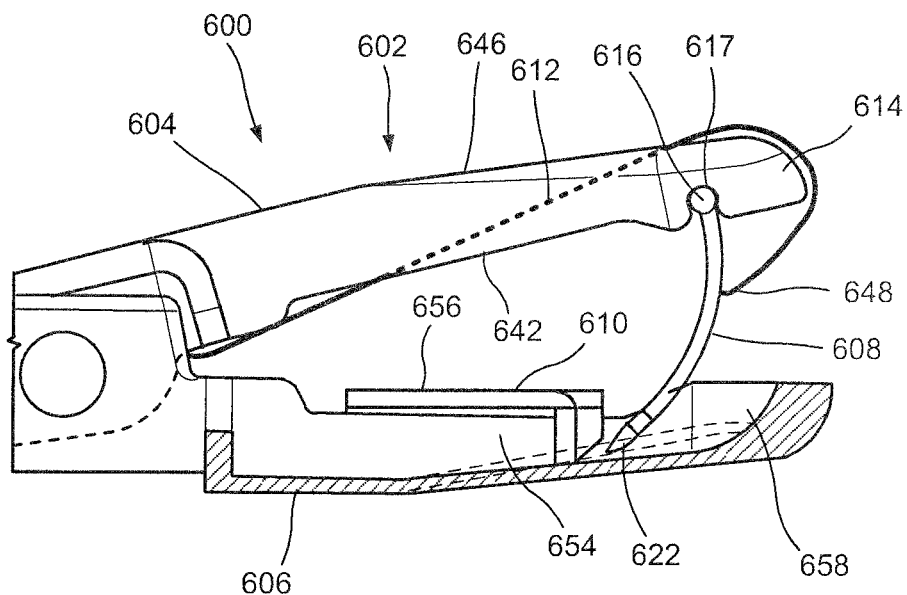
FIG. 24 shows transparent side view of the device of FIG. 22.
Figure 25:
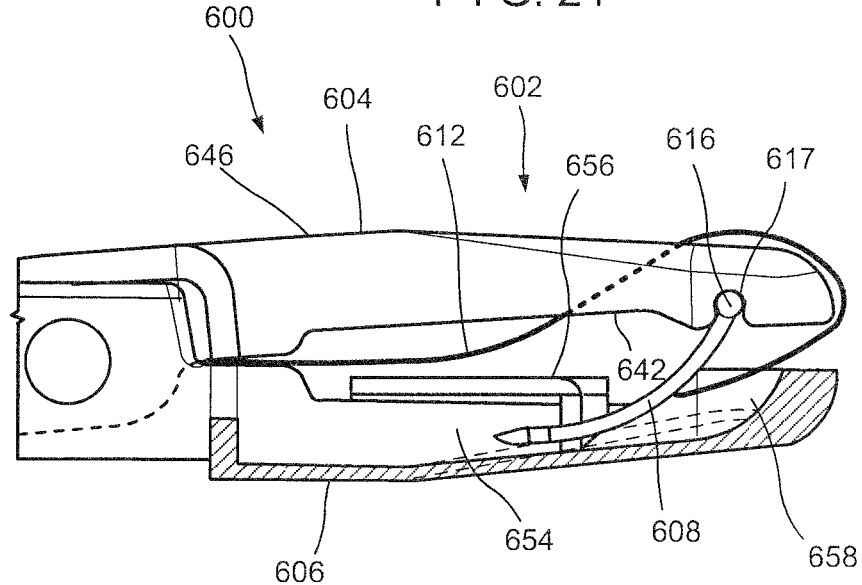
FIG. 25 shows another transparent side view of the device of FIG. 22.

The device 600 may be used in a manner substantially similar to the device 100 described above. In particular, the clip 602 is inserted into a living body to the tissue opening to be treated in the preloaded insertion configuration shown in FIG. 22. Upon reaching the tissue opening, the clip 602 is moved toward the open configuration such that distal ends 614, 615 of the arms 604, 606 are separated from one another. The needle 608 is then pivoted about the hinge 616 to the firing position, shown in FIG. 23, by tensioning the suture 612 connected thereto (i.e., drawing the suture 612 proximally relative to the clip 602) so that the second end 622 of the needle 608 extends toward the second arm 606. The clip 602 is positioned adjacent to the first portion of tissue with the first portion of tissue is received between the second end 622 of the needle 608 and the second arm 606. Once the clip 602 is positioned over the first portion of tissue, as desired, the clip 602 is moved toward the closed configuration such that the needle 608 is moved toward the second arm 606, piercing the first portion of tissue and sliding into the longitudinal recess 654 of the second arm 606. As the needle 608 is received within the longitudinal recess 654, the needle 608 comes into contact with the curved surface 658 thereof, as shown in FIG. 24, to be guided along a length thereof. Thus, the needle 608 pivots about the hinge 616 as the needle 608 is received proximally through the longitudinal recess 654, as shown in FIG. 25.

When the needle 608 is received within the longitudinal recess 654, the restraining tabs 656 lock the needle 608 therein such that the needle 608 cannot be disengaged from the second arm. A force of the engagement between the needle 608 and the restraining tabs 656 is greater than a force of the engagement between the hinge 616 and the recess 617 so that moving the clip 602 toward the open configuration causes the hinge 616 to be disengaged from the first arm 604 while the needle 608 remains locked to the second arm 606, as shown in FIGS. 26 and 27. Thus, as the clip 602 is moved toward the open configuration, the suture 612 is drawn through the first portion of tissue.

After passing the suture 612 through the first portion of tissue, the clip 602 is positioned adjacent to the second portion of tissue, creating slack in the suture 612 as the clip 602 is moved to a desired position relative to the second portion of tissue. When the second portion of tissue has been received between the first and second arms 604, 606, the clip 602 may be moved toward the closed configuration to grip the second portion of tissue therebetween. Similarly to the devices 100, 200 described above, the suture 612 may then be tensioned to draw the first portion of tissue toward the second portion of tissue, thereby closing the tissue opening. The clip 602 may be locked in the closed configuration, similarly to the clips 102, 202 described above in regard to the devices 100, 200. Locking the clip 602 in the closed configuration may wedge and cut the suture 612 via, for example, a wedge and cutting feature along an interior of the capsule, so that the clip 602 and a distal portion of the suture 612 may be deployed within the body.

Figure 28:
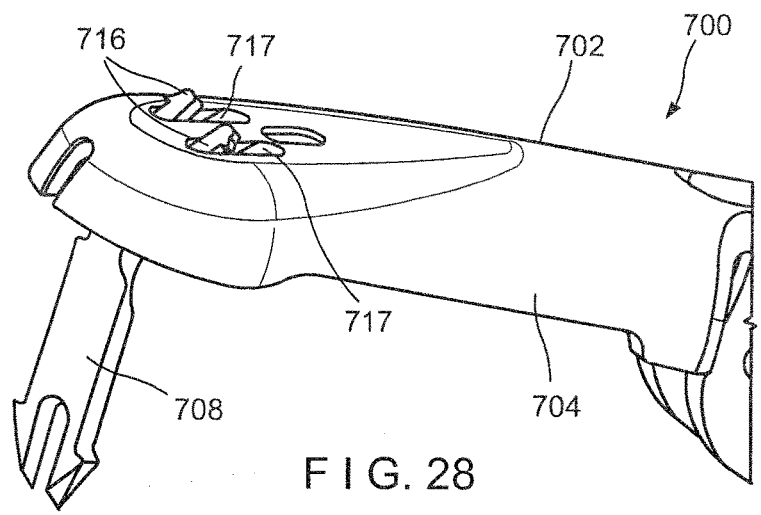
FIG. 28 shows a portion of a clip according to another exemplary embodiment.

As shown in FIG. 28, a device 700 according to another exemplary embodiment may be substantially similar to the device 600 described above except as discussed below. Rather than being coupled to a first arm 704 of a clip 702 via a hinge, however, a needle 708 of the device 700 is coupled to the first arm 704 via tabs 716 extending therefrom and engaged within correspondingly shaped slots 717 in the first arm 704. The tabs 716 and corresponding slots 717 are configured to permit movement (e.g., pivoting) of the needle 708 relative to the first arm 704 similarly to the device 600 described above. The tabs 716 remain engaged with the slots 717 until the needle 708 is received within the engagement feature along a second arm (not shown) of the clip 702.

Figure 29:
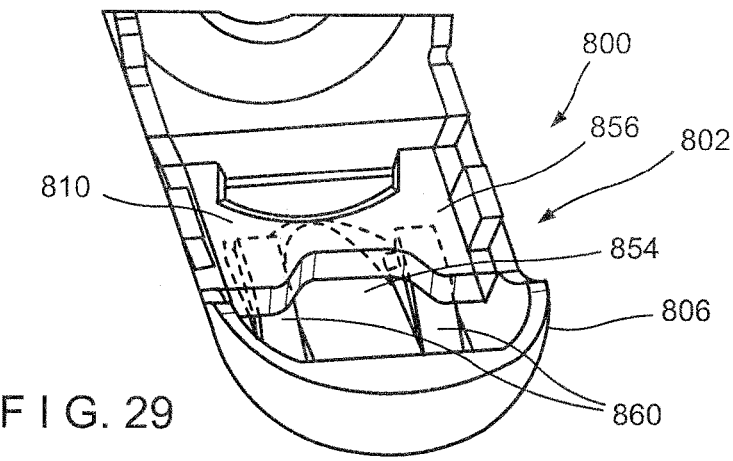
FIG. 29 shows a perspective view of a portion of a clip according to yet another exemplary embodiment.
Figure 30:
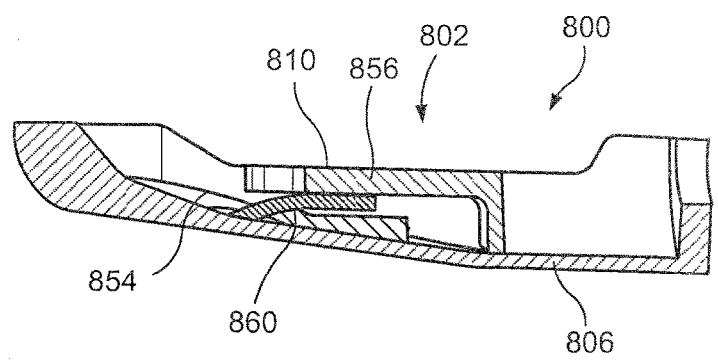
FIG. 30 shows a transparent side view of the portion of the clip of FIG. 29.

As shown in FIGS. 29-30, a device 800 may be substantially similar to the device 600 described above except as discussed below. A second arm 806 of a clip 802 of the device 800, however, includes an engagement feature 810 that further includes an elastic member 860 in addition to a longitudinal recess 854 and retaining tabs 856. The elastic element 860 extends within the longitudinal recess 845 and may be configured as a leaf spring. In particular, the elastic element 860 is biased in capture configuration in which the elastic member 860 extends into the longitudinal recess 854. Thus, when a needle, which may be substantially similar to any of the needles described herein (e.g., needle 608, needle 708) extends into the longitudinal recess 854, the elastic element 860 is deflected to permit the needle to be received therein. Once the needle is received within the longitudinal recess 854, the elastic element 860 reverts toward the biased configuration to retain the needle in the longitudinal recess 854 by pushing the needle against the retaining tabs 856.

Figure 31:
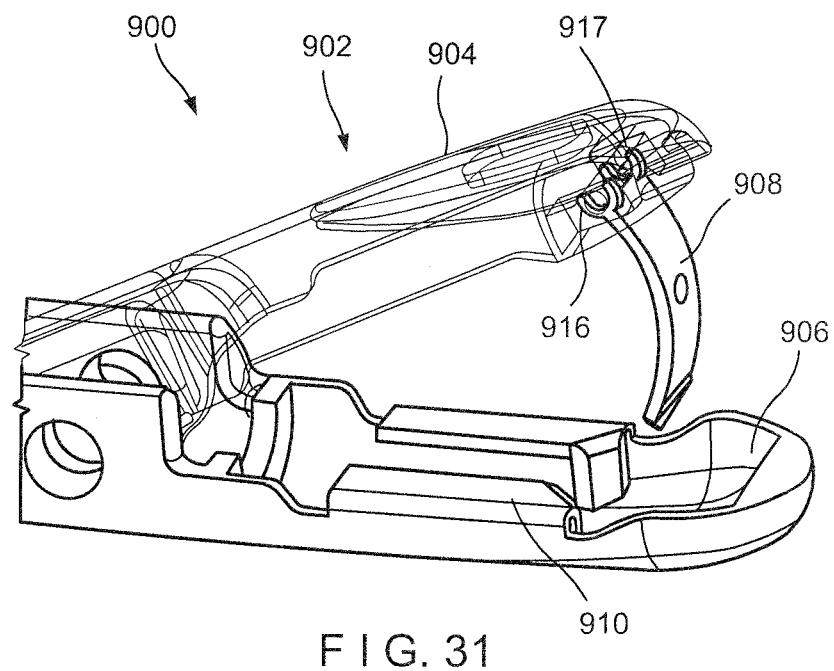
FIG. 31 shows a partially transparent perspective view of a device according to another exemplary embodiment.

According to another example, as shown in FIG. 31, a device 900 may be substantially similar to the devices 600-800 described above except as discussed below. A needle 908, however, may be pivotally coupled to a first arm 904 of a clip 902 via a C-Shaped connector 916 at an end of the needle 908, which is mounted over a pin 917 extending across a distal portion of the first arm 904. The C-shaped connector 916 and the pin 917 together create a hinge mechanism so that the needle 908 may be pivoted about the pin 917 between a preloaded insertion configuration and a firing position, as described above in regard to the device 600. The C-shaped connector 916 also permits the needle 908 to disengage the first arm 904, once the needle engages an engagement feature 910 of the second arm 906.

Figure 32:
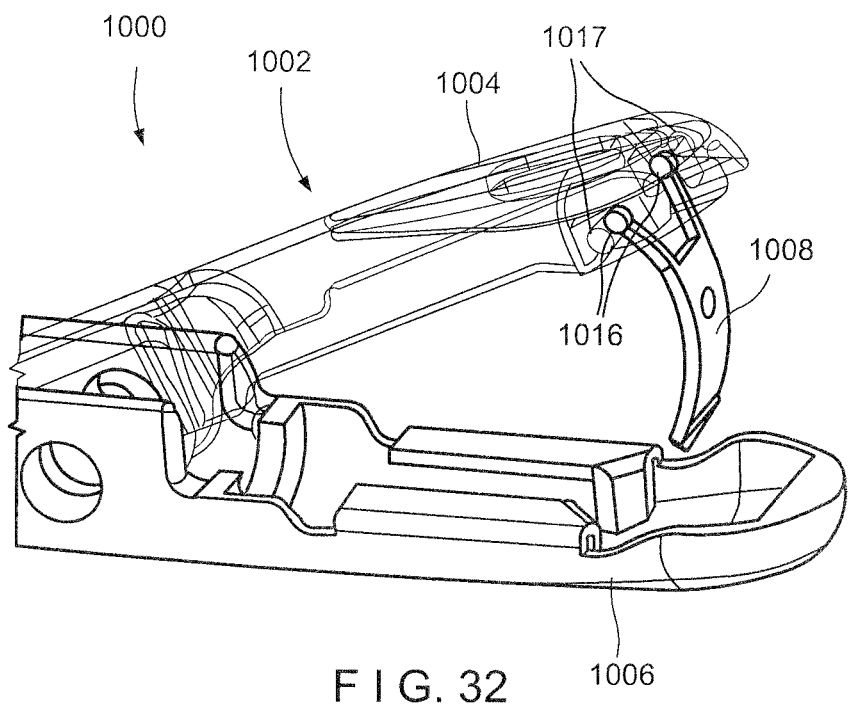
FIG. 32 shows a partially transparent perspective view of a device according to yet another exemplary embodiment.

A device 1000, as shown in FIG. 32, may also be substantially similar to the devices 600-800 except as discussed below and comprises a clip 1002 including first and second arms 1004, 1006. A needle 1008 is coupled to the first aim 1004, however, via a ball-shaped connectors 1016 at an end thereof, which are received within corresponding shaped recess 1017 within the first arm 1004. The ball-shaped connectors 1016 permits the needle 1008 to pivot with respect to the first arm between a preloaded insertion configuration and a firing position. Although the above embodiments of the devices 600-1000 describe particular examples of a pivotal connection between a needle and an arm of a clip, the needle may be connected to the arm in any of a number of different ways so long as the needle is releasably coupled to the arm and permits a pivotal motion of the needle relative to the arm.

While embodiments have been described above, a number of modifications and changes may be made without departing from the scope of the disclosure. Thus, it is intended that the present disclosure cover modifications and variations provided that they come within the scope of the appended claims and their equivalents.

What is claimed is:

1. A device for treating a tissue opening, comprising:
   a proximal portion including an elongated flexible member;
   a capsule releasably coupled to a distal end of the flexible member, the capsule extending longitudinally from a proximal end to a distal end and including a lumen extending therethrough;
   a clip including a pair of arms movably housed within the lumen of the capsule such that the pair of arms are movable between an open configuration and a closed configuration, the pair of arms being biased toward the open configuration such that when the pair of arms are moved distally with respect to the capsule, distal ends of the pair of arms are separated from one another to receive target tissue therebetween;
   a suture extending along a first one of the pair of arms and including a loop at a distal end thereof, the loop extending across an opening extending laterally through the first one of the pair of arms; and
   a suture grabbing element extending laterally from a second one of the pair of arms toward the first one of the pair of arms and including a hook so that, when the pair of arms are moved toward the closed configuration, the hook extends through the opening in the first one of the pair of arms to grab the loop extending across the opening to draw the distal end of the suture from the first one of the pair of arms toward the second one of the pair of arms.

2. The device of claim 1, wherein the first one of the pair of arms includes a notch in communication with the opening so that the loop is received within the notch to extend across the opening.

3. The device of claim 1, wherein the notch extends one of along an interior surface of the first one of the pair of arms and proximally from a distal edge of the first one of the pair of arms.

4. The device of claim 1,
   wherein the pair of arms are configured to be locked relative to the capsule in the closed configuration.

5. The device of claim 1, wherein the capsule includes a wedge feature wedging the suture between the wedge feature and a portion of one of the pair of arms, when the arms are locked within the capsule, so that the suture is restrained from distal translation.

6. The device of claim 1, wherein the capsule further includes a cutting feature cutting a portion of the suture extending proximally of a wedged portion of the suture.

7. The device of claim 1, wherein the first one of the pair of arms includes a second opening and the second one of the pair of arms includes a wedge element extending laterally therefrom toward the first one of the pair of arms so that, when the pair of arms are locked within the capsule, the wedge element extends through the second opening to wedge the suture between the wedge element and an edge of the second opening.

8. A device for treating a tissue opening, comprising:
   a proximal portion including an elongated flexible member;
   a capsule releasably coupled to a distal end of the flexible member, the capsule extending longitudinally from a proximal end to a distal end and including a lumen extending therethrough;

a clip including pair of arms movably housed within the lumen of the capsule such that the pair of arms are movable between an open configuration and a closed configuration, the pair of arms being biased toward the open configuration such that when the pair of arms are moved distally with respect to the capsule, distal ends of the pair of arms are separated from one another to receive target tissue therebetween;

a needle extending from a first end pivotally connected to a first one of the pair of arms via a releasable connection to a second end, the needle pivotal relative to the first one of the pair of arms between an insertion configuration, in which the second end is moved toward the first one of the pair of arms, and a firing position, in which the second end extends laterally toward a second one of the pair of arms, so that, when the pair of arms are moved toward the closed configuration in the firing position, the needle engages an engaging feature along a second one of the pair of arms, the releasable connection releasing when the pair of arms are moved toward the open configuration after the needle has engage the engaging feature; and a suture extending through a portion of the device such that a distal end thereof is connected to the needle.

9. The device of claim 8, wherein the needle is curved along a length thereof.

10. The device of claim 8, wherein the engagement feature includes a longitudinal recess extending through a portion of the second one of the pair of arms and retaining tabs extending over a portion thereof to prevent disengagement of the needle therefrom once the needle has been received therein.

11. The device of claim 10, wherein the engagement feature further includes a curved surface extending along a distal portion of the longitudinal recess for guiding the needle thereinto.

12. The device of claim 8,
wherein the pair of arms are configured to be locked relative to the capsule in the closed configuration.

13. The device of claim 8, wherein the capsule includes a wedge feature along an interior surface thereof for locking the suture relative to the clip when the clip is in a locked configuration and a cutting feature for cutting a portion of the suture proximal of a wedged portion of the suture.

14. A method for treating a tissue opening, comprising:
inserting a clip to a target area within a patient body, the clip including a pair of arms housed within a capsule and movable between an open configuration in which distal ends of the pair of arms are separated from one another and a closed configuration in which distal ends of the pair of arms are drawn toward one another to grip tissue received therebetween, and a suture extending along a first one of the pair of arms and including a loop at a distal end thereof, the loop extending across an opening extending laterally through the first one of the pair of arms;

positioning the pair of arms over a first portion of tissue along a tissue opening with the clip in the open configuration such that the first portion of tissue is received between the distal ends of the pair of arms;

moving the clip toward the closed configuration by drawing the pair of arms proximally into the capsule so that a hook of suture grabbing element extending laterally from a second one of the pair of arms extends through the first portion of tissue and into the opening in the first one of the pair of arms to grab the loop extending across the opening; and moving the pair of arms to the open configuration by moving the pair of arms distally relative to the capsule such that the suture grabbing element is retracted from the first portion of tissue so that the suture is passed through the first portion of tissue.

15. The method of claim 14, further comprising:
after moving the pair of arms to the open configuration with the suture passed through the first portion of tissue, positioning the pair of arms over a second portion of tissue along the tissue opening substantially opposing the first portion with the clip in the open configuration with the second portion of tissue is received between the distal ends of the pair of arms; and moving the pair of arms to the closed configuration such that the pair of arms grip the second portion of tissue between distal ends of thereof.

16. The method of claim 15, further comprising:
pulling the suture proximally relative to the clip to draw the first portion of tissue toward the second portion of tissue.

17. The method of claim 16, further comprising:
locking the clip in the closed configuration.

18. The method of claim 17, wherein locking the clip includes locking the suture relative to the clip and cutting a portion of the suture extending proximally from the clip.

* * * * *